United States Patent
Allian et al.

(10) Patent No.: US 12,365,682 B2
(45) Date of Patent: Jul. 22, 2025

(54) PROCESS TO MAKE GLP1 RA AND INTERMEDIATES THEREFOR

(71) Applicants: ELI LILLY AND COMPANY, Indianapolis, IN (US); CHUGAI SEIYAKU KABUSHIKI KAISHA, Shizuoka (JP)

(72) Inventors: Ayman D. Allian, Carmel, IN (US); Kenneth Derek Berglund, Fishers, IN (US); Kevin Paul Cole, Indianapolis, IN (US); Ashlee Jeanette Davis, Indianapolis, IN (US); Molly Hess, Avon, IN (US); Adriana Jemison, Indianapolis, IN (US); Mark Steven Kerr, Indianapolis, IN (US); Audrey Grace Mack, Indianapolis, IN (US); Xavier A. Ortiz-Medina, Noblesville, IN (US); David Michael Remick, Fishers, IN (US); Derek Robert Starkey, Avon, IN (US); Radhe Krishan Vaid, Carmel, IN (US); Qiang Yang, Zionsville, IN (US); Fumiki Kawagishi, Kanagawa (JP); Takashi Emura, Kanagawa (JP); Satoshi Tsuchiya, Kanagawa (JP); Manabu Wadamoto, Kanagawa (JP); Minoru Yamawaki, Kanagawa (JP)

(73) Assignees: ELI LILLY AND COMPANY, Indianapolis, IN (US); CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/823,214

(22) Filed: Sep. 3, 2024

(65) Prior Publication Data

US 2025/0042899 A1 Feb. 6, 2025

Related U.S. Application Data

(63) Continuation of application No. PCT/US2023/084487, filed on Dec. 18, 2023.

(60) Provisional application No. 63/433,515, filed on Dec. 19, 2022.

(51) Int. Cl.
*C07D 471/04* (2006.01)

(52) U.S. Cl.
CPC .................. *C07D 471/04* (2013.01)

(58) Field of Classification Search
CPC ................................... C07D 471/04
See application file for complete search history.

(56) References Cited

U.S. PATENT DOCUMENTS 10,858,356 B2 *  12/2020  Yoshino ................ A61P 25/16
2019/0225604 A1     7/2019  Yoshino et al.

FOREIGN PATENT DOCUMENTS

JP      2019099571      6/2019

OTHER PUBLICATIONS

International Search Report and Written Opinion of PCT/US2023/084487 (filed on Dec. 18, 2023 by Eli Lilly and Company), International Search Completed on May 21, 2024, Mailed on Jun. 7, 2024 by the European Patent Office, 11 pages.

* cited by examiner

*Primary Examiner* — Clinton A Brooks
*Assistant Examiner* — Josmalen M. Ramos-Lewis
(74) *Attorney, Agent, or Firm* — Yong Zhao

(57) ABSTRACT

The present invention relates to the synthesis of 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl ]-4-methyl-6,7-dihydro-4H-pyrazolo [4,3-c] pyridine-5-carbonyl] indol-1-yl]-2-methylcyclopropyl]-4H-1,2,4-oxadiazol-5-one, or a salt thereof, and related synthetic intermediate compounds.

20 Claims, No Drawings

PROCESS TO MAKE GLP1 RA AND INTERMEDIATES THEREFOR

CROSS REFERENCE TO RELATED APPLICATIONS

The instant application is a continuation application of pending application No. PCT/US2023/084487 filed Dec. 18, 2023, which claims priority to US Provisional Application No. 63/433,515 filed Dec. 19, 2022.

TECHNICAL FIELD

Disclosed herein is a process for the synthesis of a GLP-1 receptor agonist, 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl] indol-1-yl]-2-methylcyclopropyl]-4H-1,2,4-oxadiazol-5-one, or a salt thereof (herein, GLPIRA), or a hydrate of the salt.

BACKGROUND

GLPIRA was described and claimed in U.S. Pat. No. 10,858,356.

U.S. Pat. No. 10,858,356 describes a synthetic process for preparing GLPIRA. Nevertheless, there is a need for an alternative process for preparing the compound. The process described herein provides one or more benefits over the known process as it goes through different intermediates. In one embodiment, the instant process is more robust and efficient. In one embodiment, the instant process is more scalable. In one embodiment, the instant process provides a higher yield.

DESCRIPTION

GLPIRA may be prepared as a pharmaceutically acceptable salt. One salt of GLPIRA is a hemi-calcium salt of 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl] indol-1-yl]-2-methylcyclopropyl]-4H-1,2,4-oxadiazol-5-one (herein "GLPIRA ½ Ca$^{2+}$") with the structure as shown below.

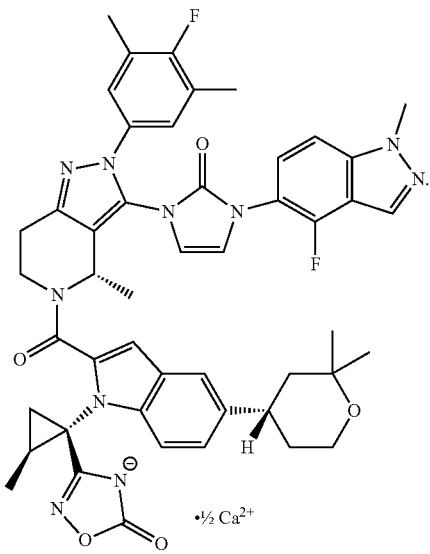 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[n-]4)C[C@@H]2C)CC3)cc(C)c1F]

GLPIRA may be prepared as a hydrate of a pharmaceutically acceptable salt. One hydrate of GLPIRA is a hemi-calcium hydrate of 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c] pyridine-5-carbonyl] indol-1-yl]-2-methylcyclopropyl]-4H-1,2,4-oxadiazol-5-one ("GLPIRA ½ Ca$^{2+}$ hydrate").

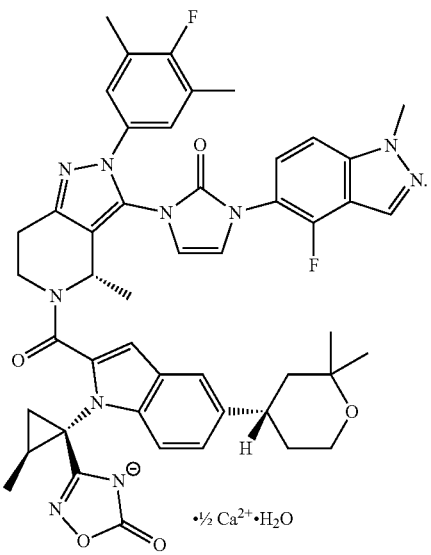 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[n-]4)C[C@@H]2C)CC3)cc(C)c1F]

In one embodiment, disclosed herein is a process for making compound 6 of the following structure:

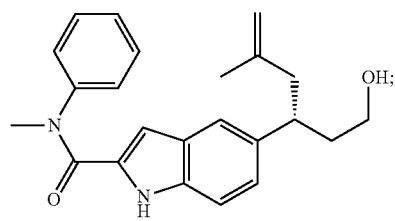 [SMILES: C=C(C)C[C@H](CCO)c1ccc2[nH]c(C(=O)N(C)c3ccccc3)cc2c1]

comprising multi-step chemical reactions starting from compound 1 of the following structure:

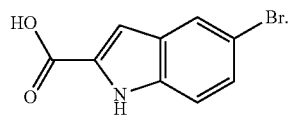 [SMILES: O=C(O)c1cc2cc(Br)ccc2[nH]1]

In one embodiment, the above process comprises multi-step chemical reactions starting from the following compound:

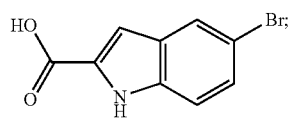 [SMILES: O=C(O)c1cc2cc(Br)ccc2[nH]1]

going through compound 5:

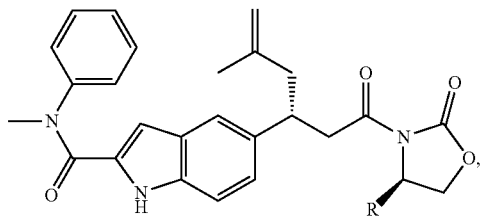

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl;

and arriving at compound 6:

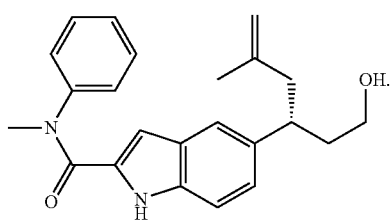 [SMILES: C=C(C)C[C@H](CCO)c1ccc2[nH]c(C(=O)N(C)c3ccccc3)cc2c1]

In one embodiment, R is phenyl or benzyl. In another embodiment, R is phenyl. In another embodiment, R is benzyl.

In one embodiment, the above process comprises a reaction step converting compound 1 to compound 2 as shown below:

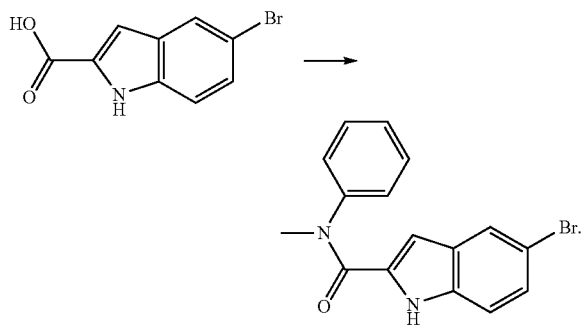

In one embodiment, the above process further comprises a reaction step converting compound 2 to compound 3 as shown below:

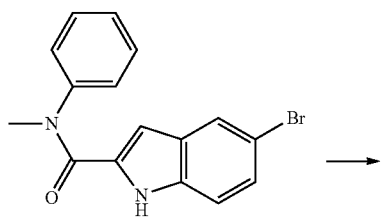

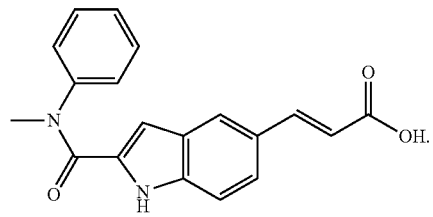

In one embodiment, the above process further comprises a reaction step converting compound 3 to compound 4 as shown below:

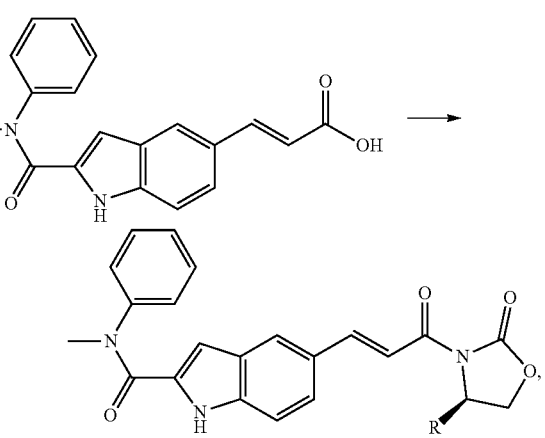

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl phenyl or benzyl. In one embodiment, R is phenyl or benzyl.

In one embodiment, R is phenyl. In another embodiment, R is benzyl.

In one embodiment of the reaction from compound 3 to compound 4, the process comprises a reaction of compound 3 with CDI in a solvent, followed by a coupling with (R)-4-benyl-2-oxazolidone in the presence of 1,8-doazabi-cyclo[5.4.0]undec-7-ene in a solvent.

In one embodiment of the reaction from compound 3 to compound 4, the process comprises a reaction of compound 3 with CDI in a solvent, followed by a coupling with (R)-4-phenyl-2-oxazolidone in the presence of 1,8-doazabi-cyclo[5.4.0]undec-7-ene in a solvent.

In one embodiment, the above process further comprises a reaction step converting compound 4 to compound 5 as shown below:

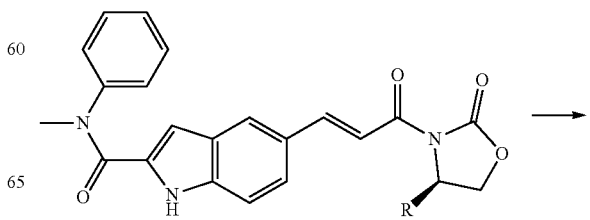

-continued

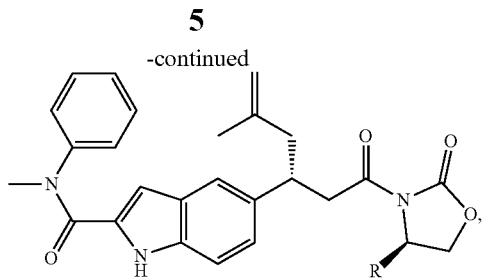

wherein R is phenyl or benzyl. In one embodiment, R is phenyl. In another embodiment, R is benzyl.

In one embodiment of the reaction from compound 4 to compound 5, the process comprises a copper mediated addition of 2-methyl allyl magnesium chloride in the presence of lithium chloride to compound 4 to give compound 5.

In one embodiment, the above process further comprises a reaction step converting compound 5 to compound 6 as shown below:

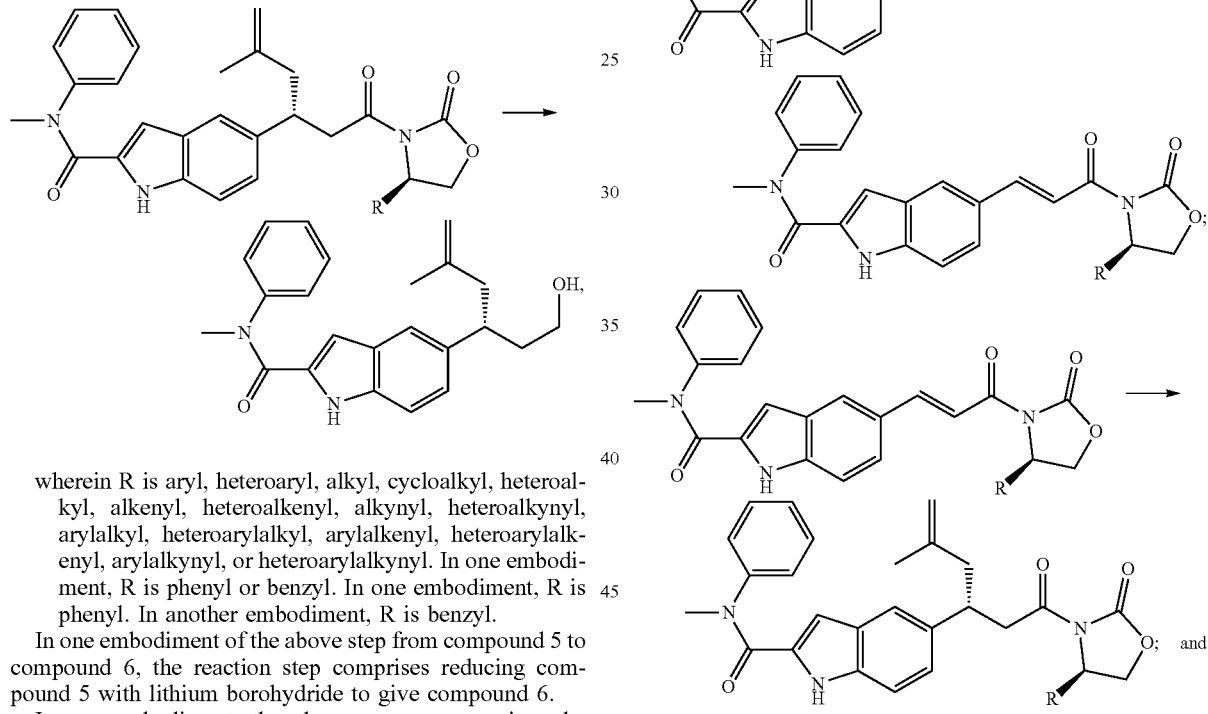

wherein R is aryl, heteroaryl, alkyl, cycloalkyl, heteroalkyl, heteroalkenyl, alkynyl, heteroalkynyl, arylalkyl, heteroarylalkyl, arylalkenyl, heteroarylalkenyl, arylalkynyl, or heteroarylalkynyl. In one embodiment, R is phenyl or benzyl. In one embodiment, R is phenyl. In another embodiment, R is benzyl.

In one embodiment of the above step from compound 5 to compound 6, the reaction step comprises reducing compound 5 with lithium borohydride to give compound 6.

In one embodiment, the above process comprises the following multi-step reactions starting from compound 1 to arrive at compound 6:

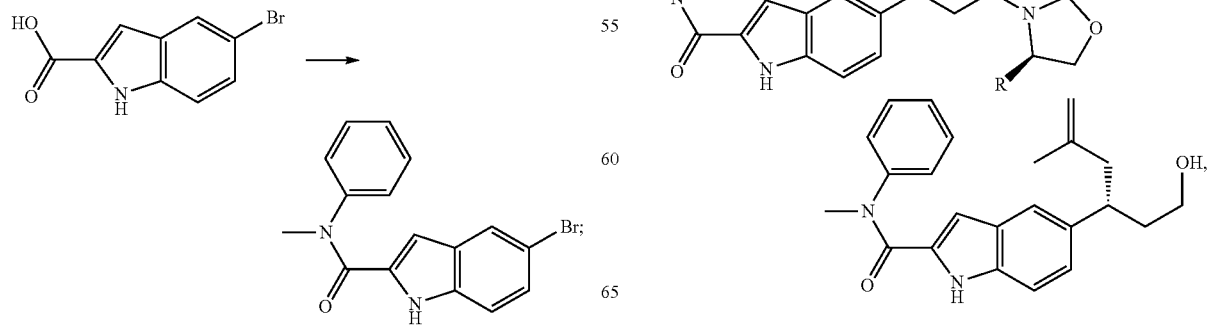

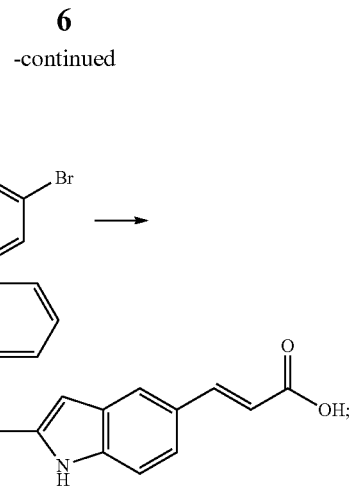

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl. In one embodiment, R is phenyl or benzyl. In one embodiment, R is phenyl. In another embodiment, R is benzyl.

In one embodiment, disclosed herein is a process for making compound 12 of the following structure:

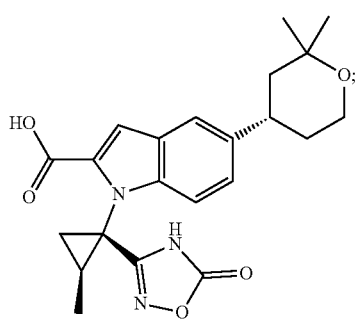 [SMILES: C[C@H]1C[C@]1(c1noc(=O)[nH]1)n1c(C(=O)O)cc2cc([C@H]3CCOC(C)(C)C3)ccc21]

comprising multi-step chemical reactions starting from compound 6 of the following structure:

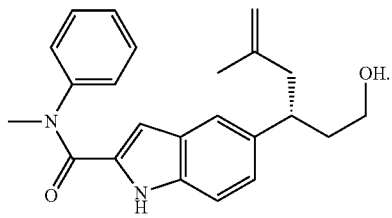 [SMILES: C=C(C)C[C@H](CCO)c1ccc2[nH]c(C(=O)N(C)c3ccccc3)cc2c1]

In one embodiment, the above process comprises multi-step chemical reactions starting from the following compound:

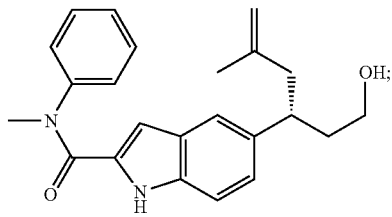 [SMILES: C=C(C)C[C@H](CCO)c1ccc2[nH]c(C(=O)N(C)c3ccccc3)cc2c1]

going through compound 7:

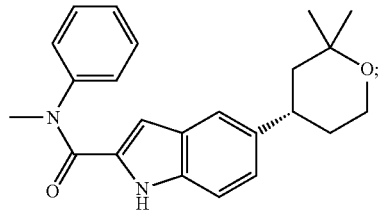 [SMILES: CN(C(=O)c1cc2cc([C@H]3CCOC(C)(C)C3)ccc2[nH]1)c1ccccc1]

going through compound 10:

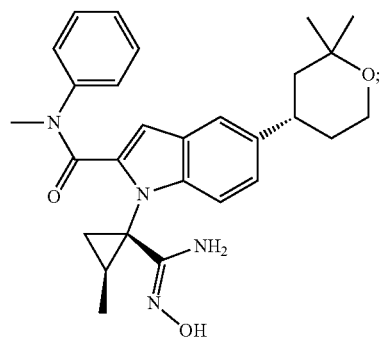 [SMILES: C[C@H]1C[C@]1(/C(N)=N/O)n1c(C(=O)N(C)c2ccccc2)cc2cc([C@H]3CCOC(C)(C)C3)ccc21]

going through compound 11:

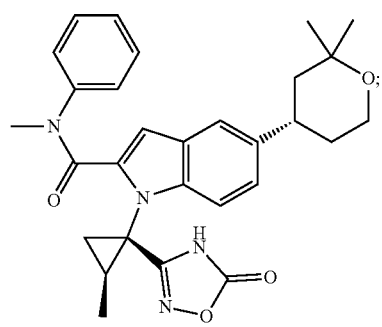 [SMILES: C[C@H]1C[C@]1(c1noc(=O)[nH]1)n1c(C(=O)N(C)c2ccccc2)cc2cc([C@H]3CCOC(C)(C)C3)ccc21]

and arriving at compound 12:

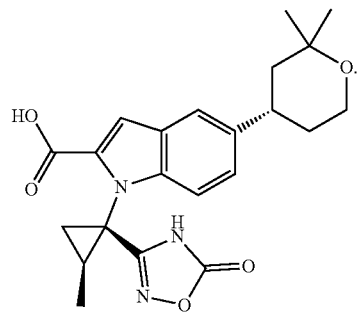 [SMILES: C[C@H]1C[C@]1(c1noc(=O)[nH]1)n1c(C(=O)O)cc2cc([C@H]3CCOC(C)(C)C3)ccc21]

In one embodiment, the above process comprises a reaction step converting compound 6 to compound 7 as shown below:

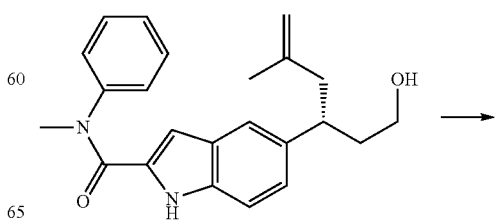

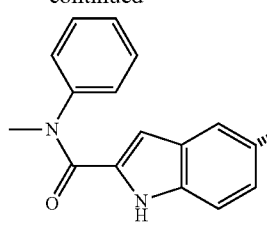

In one embodiment, the above process further comprises a reaction step converting compound 10 to compound 11 as shown below:

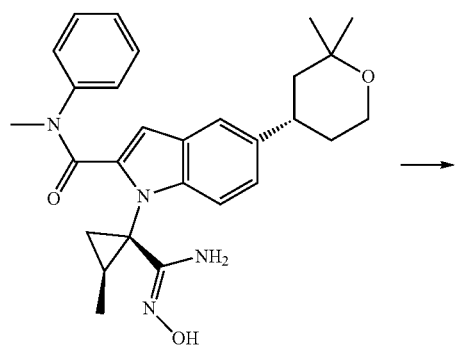

In one embodiment, the above multi-step process from compound 6 to compound 12 comprises the following reactions converting compound 6 to compound 7 and converting compound 10 to compound 11:

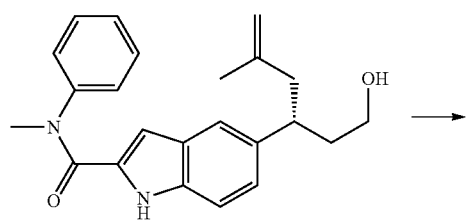

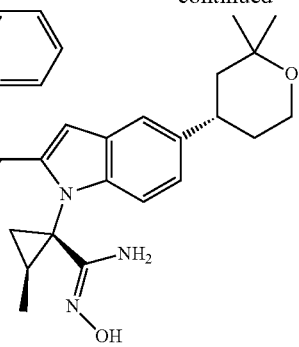

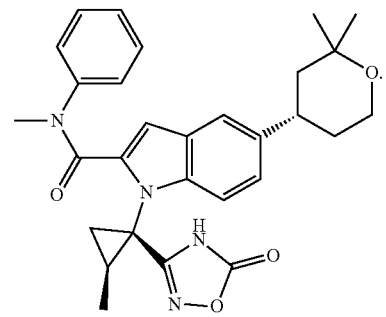

In one embodiment, disclosed herein is a process for making compound 20 of the following structure:

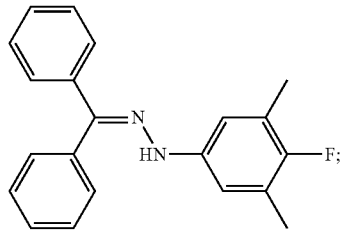 [SMILES: Cc1cc(NN=C(c2ccccc2)c2ccccc2)cc(C)c1F]

comprising multi-step chemical reactions starting from compound 19 of the following structure:

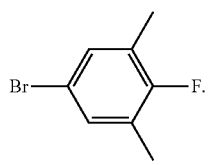

In one embodiment, the above process comprises multi-step chemical reactions starting from the following compound:

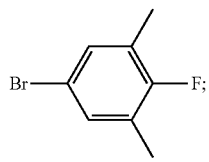

and arriving at compound 20:

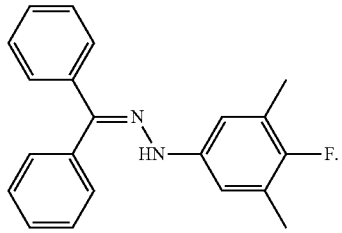 [SMILES: Cc1cc(NN=C(c2ccccc2)c2ccccc2)cc(C)c1F]

In one embodiment, the above process comprises a reaction step from compound 19 to compound 20 as shown below:

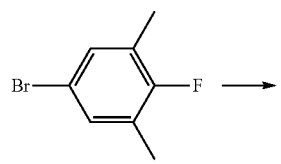

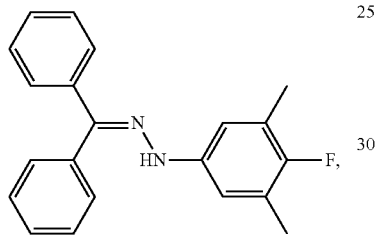

wherein the reaction step comprises a coupling reaction of compound 19 with (diphenylmethylene) hydrazine using a catalyst selected from Pd(OAc)$_2$ and Xantphos to give compound 20.

In one embodiment, the above process further comprises a reaction step converting compound 20 to compound 21 as shown below:

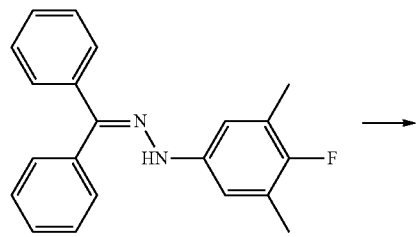

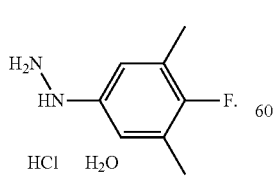

In one embodiment, the above process comprises multi-step reactions for making compound 24 starting from compound 21 as shown below:

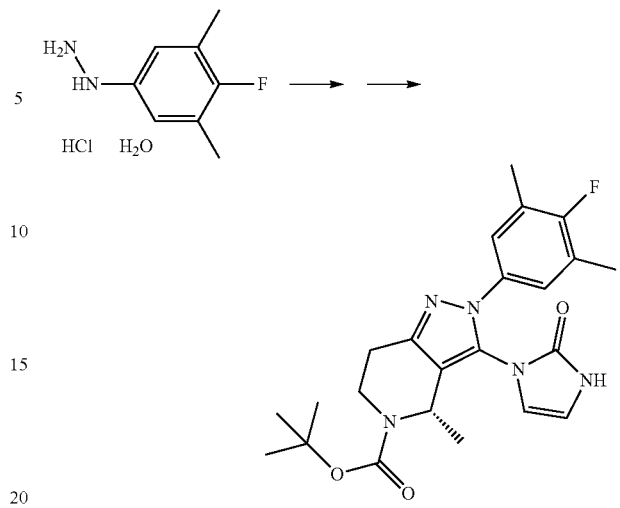

In one embodiment, disclosed herein is compound 3 of the following structure:

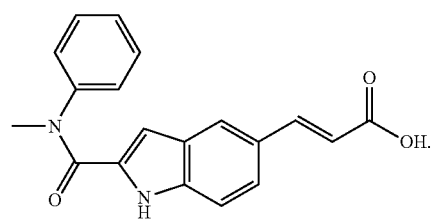 [SMILES: CN(C(=O)c1cc2cc(/C=C/C(=O)O)ccc2[nH]1)c1ccccc1]

In one embodiment, disclosed herein is compound 4 of the following structure:

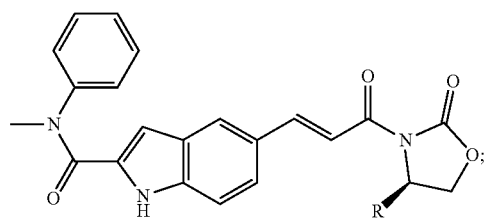

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl.

In one embodiment, disclosed herein is compound 5 of the following structure:

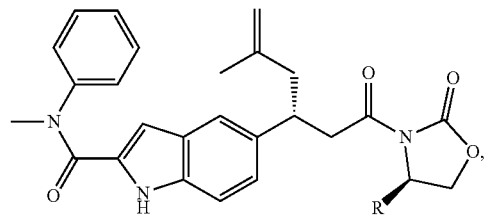

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl. In one embodiment, R is phenyl or benzyl. In one embodiment, R is phenyl. In another embodiment, R is benzyl.

In one embodiment, disclosed herein is compound 6 of the following structure:

In one embodiment, disclosed herein is compound 20 of the following structure:

In one embodiment, disclosed herein is a compound of the following structure:

Unless otherwise defined in the specification, certain abbreviations are defined as follows:
ACN—acetonitrile;
aq.—aqueous;
Bn—benzyl;
CDI—1,1'-carbonyldiimidazole;
COMU—1-cyano-2-ethoxy-2-oxoethylidenaminooxy)dimethylamino-morpholino-carbenium hexafluorophosphate;
CSTR—continuous stirred-tank reactor;
DBU—1,8-diazabicyclo [5.4.0]undec-7-ene;
DCM—dichloromethane;
DEA—diethylamine;
DIPEA—N,N-diisopropylethylamine;
DMAc—dimethylacetamide;
DMF—dimethylformamide;
DMI—1,3-dimethyl-2-imidazolidinone;
DMSO—dimethyl sulfoxide;
DSC—differential scanning calorimetry;
ESI—electrospray ionization;
EtOAc—ethyl acetate;
EtOH—ethanol and ethyl alcohol;
h—hour(s)
HATU—1-[bis(dimethylamino)methylene]-1H-1,2,3-triazolo[4,5-b]pyridinium-3-oxide hexafluorophosphate;
HPLC—high-performance liquid chromatography;
HRMS—high-resolution mass spectrometry;
IPA—isopropanol and isopropyl alcohol;
IPAc—isopropyl acetate;
KF—Karl Fischer titration;
MeOH—methanol and methyl alcohol;
2-MeTHF—2-methyltetrahydrofuran;
min—minute(s)
mp—melting point
MTBE—methyl tert-butyl ether;
NMM—N-methylmorpholine;
NMP—1-methyl-2-pyrrolidinone;
NMR—nuclear magnetic resonance;
NMT—not more than;
Ph—phenyl;
Pd(OAc)$_2$—palladium (II) acetate;
QNMR—quantitative nuclear magnetic resonance;
TBAB—tetrabutylammonium bromide;
TEA—triethylamine;
THF—tetrahydrofuran;
TOF-MS—time of flight mass spectrometer.

Scheme 1

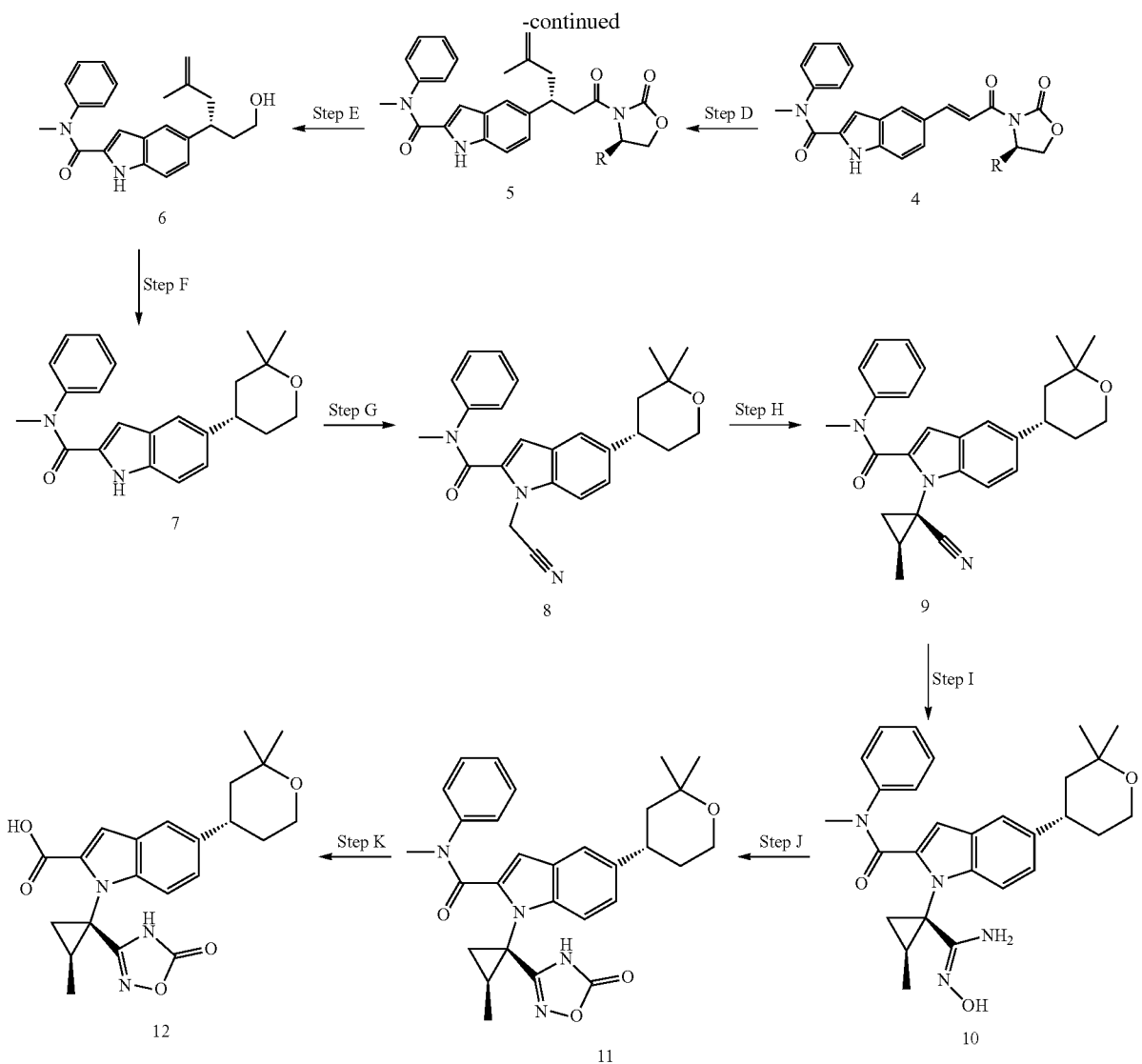

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl. In one embodiment, R is benzyl or phenyl. In one embodiment, R is phenyl. In another embodiment, R is benzyl.

Scheme 1, step A shows the formation of an acid chloride of compound 1 using oxalyl chloride in a solvent such as ACN, followed by reaction with N-methylaniline to give compound 2. There are many ways to perform an amide coupling whether by generating an acid chloride or through the use of amide coupling reagents such as SOCl2, Ac2O, PivCl, ethyl chloroformate (ECF), isobutyl chloroformate (IBCF), Boc anhydride, T3P, DCC, DIC, CDI, EDC, HATU, HBTU, TBTU, TPTU, TBTU, TPTU, Cyanuric chloride, CDMT or DMTMM. Also a variety of solvents could be used such as toluene, MTBE, THF, 2-MeTHF, DCM, EtOAc, isobutyl acetate, isopropyl acetate, dioxane, DMF, DMAc, NMP, DMI, DMSO or CPME. The reaction could be carried out at a temperature ranging from −10 to 100° C. In one embodiment, the reaction temperature was in the range of 0 to 40° C.

Step B shows a Heck coupling between compound 2 and acrylic acid to give compound 3. There are many methods to perform a Heck coupling using various catalyst ligand combinations such as tetrakis(triphenylphosphine) [Pd (PPh3)4], palladium (0)), palladium chloride (PdCl2), palladium (II) acetate [Pd(OAc)2], allylpalladium (II) chloride dimer [PdCl(C3H5)2], Pd(dppf)Cl2, and Pd(dtbpf)Cl2. A variety of solvents could be used such as toluene, MeCN, MTBE, THF, 2-MeTHF, DCM, EtOAc, isobutyl acetate, isopropyl acetate, dioxane, DMF, DMAc, NMP, DMI, DMSO, or CPME. The reaction could be carried out at a temperature ranging from −10 to 150° C. In one embodiment, the reaction temperature was 40 to 100° C.

Step C shows the reaction of compound 3 with CDI in a solvent such as ACN, followed by a coupling with an appropriate oxazolidinone in the presence of 1,8-diazabicyclo[5.4.0]undec-7-ene in a solvent such as N,N-dimethylacetamide to give compound 4. There are many additional ways to perform an amide coupling whether by generating an acid chloride or through the use of amide coupling reagents such as SOCl2, Ac2O, PivCl, ethyl chloroformate (ECF), isobutyl chloroformate (IBCF), Boc anhydride, T3P, DCC, DIC, EDC, HATU, HBTU, TBTU, TPTU, TBTU, TPTU, Cyanuric chloride, CDMT, or DMTMM. Also a variety of solvents could be used such as toluene, MTBE, THF, 2-MeTHF, DCM, EtOAc, isobutyl acetate, isopropyl acetate, dioxane, DMF, DMAc, NMP, DMI, DMSO, or CPME. The reaction could be carried out at a temperature ranging from −10 to 100° C. In one embodiment, the reaction temperature was 0 to 40° C.

The copper-mediated addition of 2-methyl allyl magnesium chloride in the presence of lithium chloride to compound 4 to give compound 5 is depicted in step D. Combinations of other Grignard reagents such as 2-methyl allyl magnesium bromide and 2-methyl allyl magnesium iodide could be used along with salts such as LiBr or LiI and Cu reagents such as CuBr or CuI and in solvents such as $Et_2O$, MTBE, THF, 2-MeTHF, or CPME. The reaction of Step D could be carried out at a temperature ranging from −80 to 20° C. In one embodiment, the reaction temperature was −60 to −10° C.

Step E shows the reduction of compound 5 with lithium borohydride to give compound 6. There are many other reducing agents such as $NaBH_4$, $BH_3$, LAH, $H_2$, DIBAl, or Red-Al and suitable solvents selected from toluene, THF, 2-MeTHF, DCM, MTBE, and CPME. Step E reaction could be carried out at a temperature ranging from −80 to 80° C. In one embodiment, the temperature was −40 to 80° C.

The cyclization of compound 6 to compound 7 using p-toluenesulfonic acid monohydrate in a solvent such as cyclopentyl methyl ether is shown in step F. This step could be performed using other acid/solvent combinations such as MsOH, TsOH, $H_2SO_4$, HCl, or TFA with toluene, MeCN, MTBE, THF, 2-MeTHF, DCM, or dioxane. Step E reaction could be carried out at a temperature ranging from −10 to 100° C. In one embodiment, the temperature was 20 to 80° C.

Step G shows the alkylation of compound 7 with chloroacetonitrile using an appropriate base such as potassium hydroxide and catalytic tetrabutylammonium chloride hydrate in a solvent such as toluene to give compound 8.

Step H shows the reaction between compound 8 and (R)-4-methyl-1,3,2-dioxathiolane 2,2-dioxide using a suitable base such as potassium bis(trimethylsilyl)amide or lithium t-butoxide in a suitable solvent such as THF to give compound 9.

The addition of hydroxylamine to compound 9 in a suitable solvent such as IPA or THF to give compound 10 is shown in step I.

The intramolecular cyclization of compound 10 using CDI and an appropriate base such as DBU in a solvent such as THE to give compound 11 is depicted in step J. This cyclization can be performed with other reagents such as DCC, DIC, EDC, phosgene, diphosgene, triphosgene, dimethylcarbonate, diethylcarbonate, PivCl, ethyl chloroformate, isobutylchloroformate, Boc anhydride, EEDQ, oxalyl chloride, $CO_2$ with other bases such as pyridine, pyrrolidine, pyrrole, triethylamine, DIPEA, methylamine, diethylamine, ethyldimethylamine, imidazole, diisopropylamine, Barton's base, NaOH, NaOMe, NaOEt, NaOtBu in other solvents such as 2-MeTHF, toluene, IPA, isopropyl acetate, DMF, DMI, EtOAc, EtOH, MeOH, acetonitrile, DMAc, dioxane, iBuOAc, MTBE, DCM, CPME, DMSO, NMP at a temperature ranging from 0 to 150° C. In one embodiment, the temperature was 5 to 40° C.

Step K shows the hydrolysis of compound 11 using a base such as sodium t-butoxide in the presence of water in a solvent such as DMI followed by acidification with aqueous $H_2SO_4$ to give compound 12.

Scheme 2

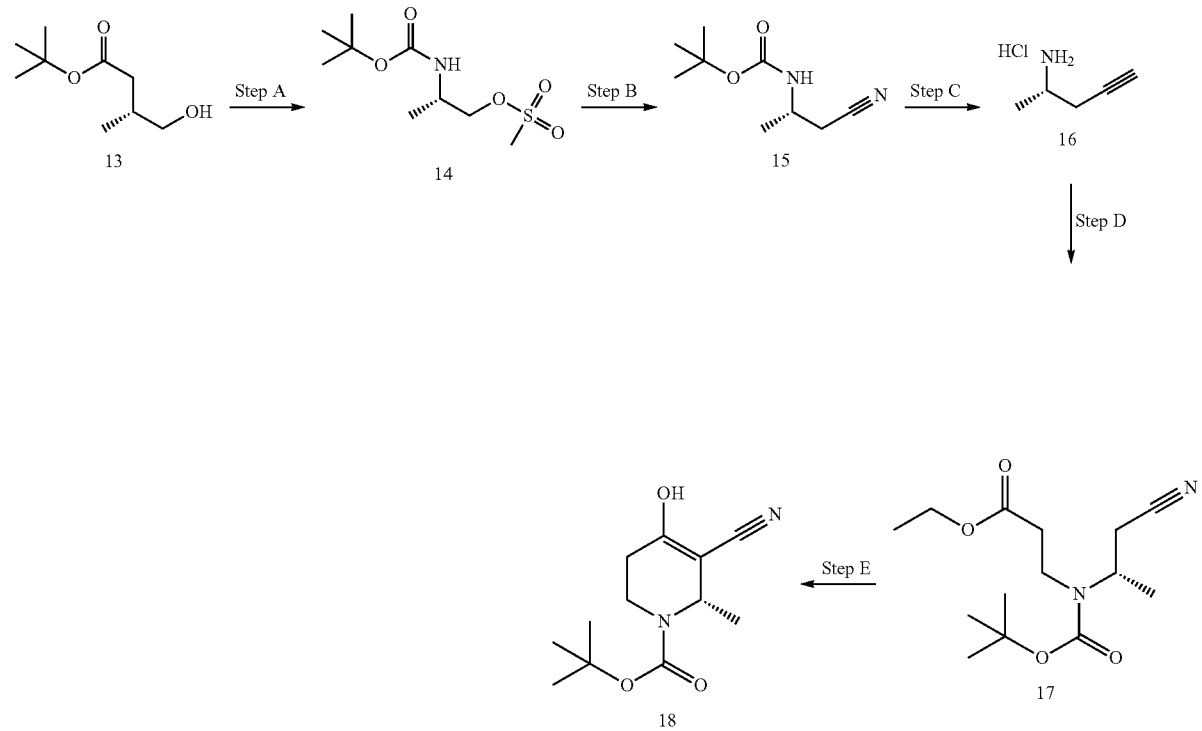

Scheme 2, step A shows the reaction of compound (13) with methane sulfonic anhydride using a base such as TEA in a solvent such as DCM to give compound 14. Step B shows a nucleophilic substitution on compound 14 using sodium cyanide and a phase transfer catalyst such as TBAB in a solvent such as DMF to give compound 15. Step C shows the acidic deprotection of compound 15 with HCl in a solvent such as DCM to give compound 16. Step D shows the addition of compound 16 to ethyl acrylate using a suitable base such as TEA in a solvent such as EtOH followed by protection with di-tert-butyl dicarbonate to give compound 17. The cyclization of compound 17 using a base such as potassium t-butoxide in a solvent such as THF to give compound 18 is shown in step E.

Scheme 3

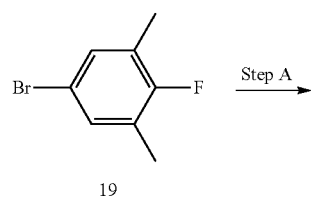

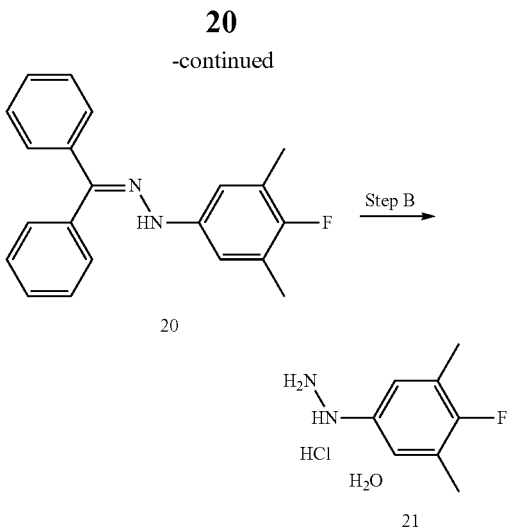

Scheme 3, step A shows the coupling of compound 19 and (diphenylmethylene) hydrazine using an appropriate catalyst/ligand system such as Pd(OAc)$_2$ and Xantphos, a base such as NaOH, and a solvent system such as tert-amyl alcohol or toluene and water to give compound 20. Step B shows the acidic deprotection of compound 20 with HCl in a solvent such as dioxane to give compound 21. Alternatively, the deprotection could be performed using acetic acid and water.

Scheme 4

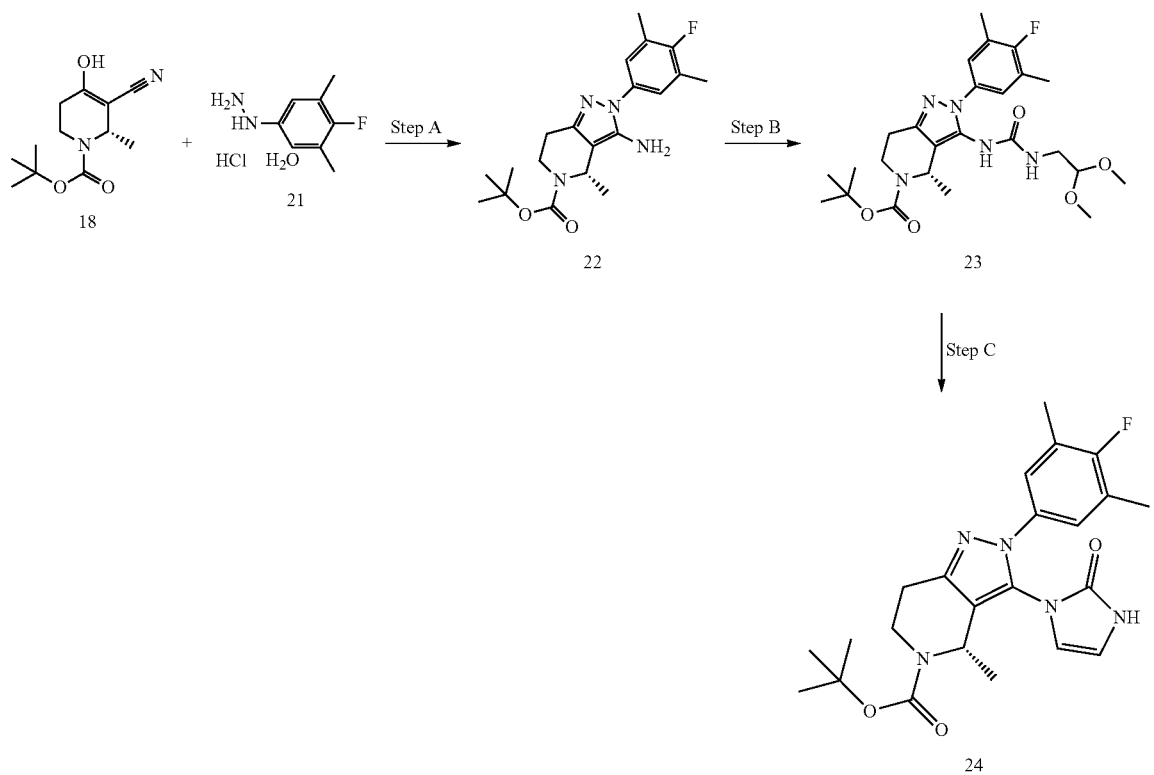

Scheme 4, step A shows the coupling of compounds 18 and 21 and subsequent cyclization to give compound 22 using a suitable base such as NMM in a solvent such as NMP. Step B shows the addition of (N-(2,2-dimethoxyethyl)-1H-imidazole-1-carboxamide) to compound 22 using a base such as potassium t-butoxide in a solvent such as DMAc to give compound 23. Step C shows the intramolecular cyclization of compound 23 using methanesulfonic acid in a solvent such as THF to give compound 24.

Scheme 5

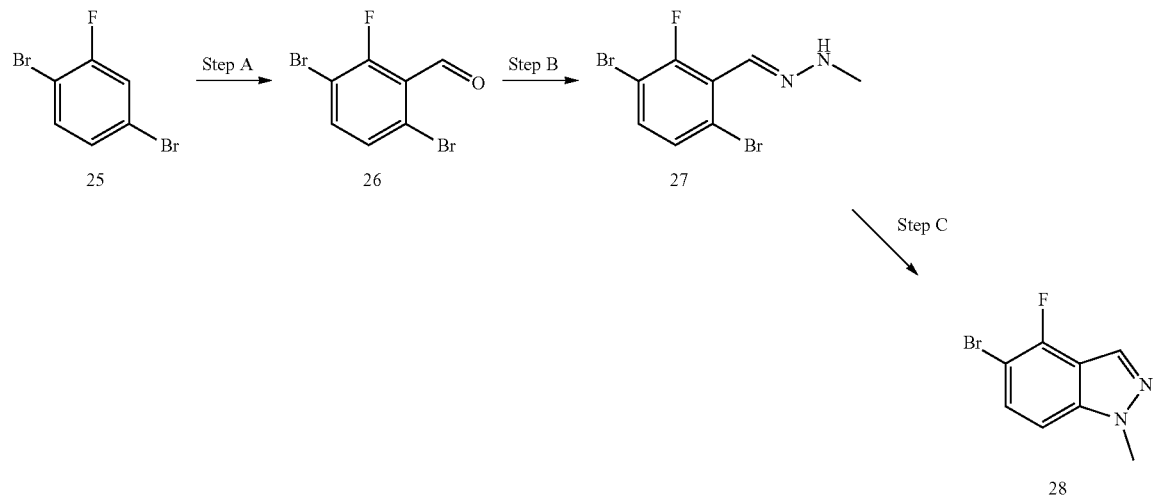

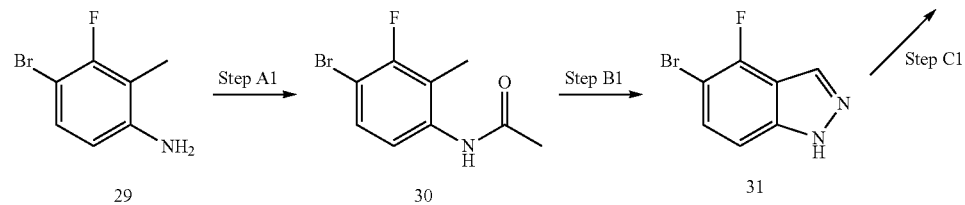

Scheme 5, step A shows the lithiation of compound 25 and subsequent reaction with DMF in a solvent such as 2-MeTHF to give compound 26. Step B shows the addition of methylhydrazine to compound 27 in a solvent such as EtOH to give compound 27. The intramolecular cyclization of compound 27 using CuCl and a base such as DBU in a solvent such as DMI to give compound 28 is shown in step C.

An alternative route to compound 28 begins with step A1 where compound 29 is treated with acetic anhydride in a solvent such as toluene to give compound 30. Step B1 shows the cyclization of compound 30 using isoamyl nitrite in a solvent such as toluene to give compound 31. Step C1 shows the methylation of compound 31 using methyl iodide, a base such as potassium carbonate, and a solvent such as DMF to give compound 28.

Scheme 6
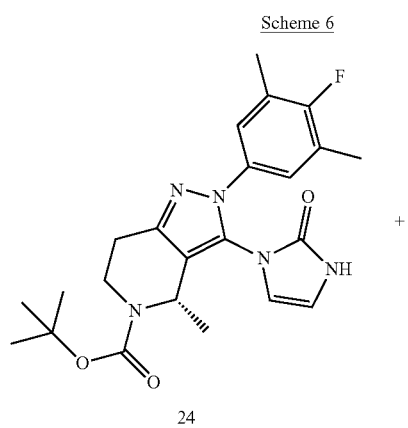
24
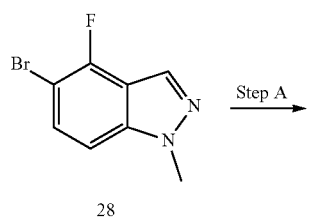
28
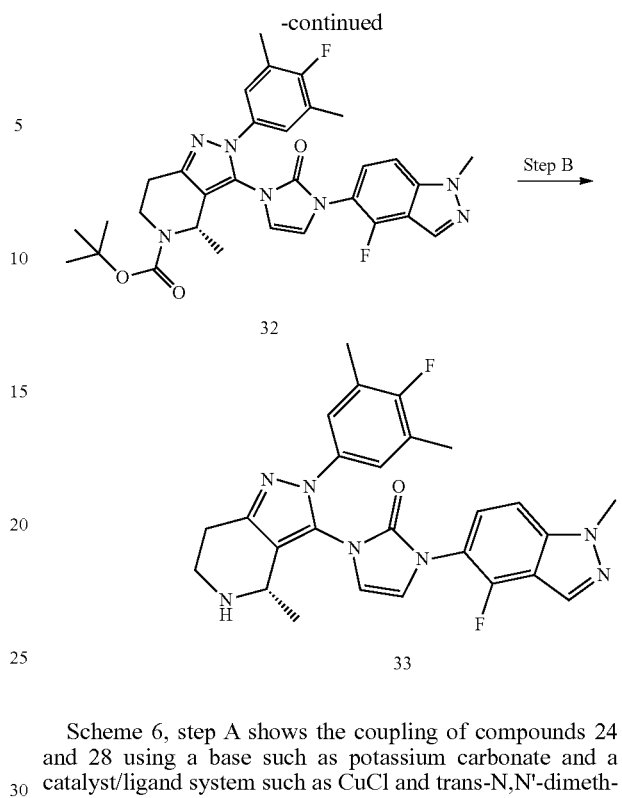
Scheme 6, step A shows the coupling of compounds 24 and 28 using a base such as potassium carbonate and a catalyst/ligand system such as CuCl and trans-N,N'-dimethylcyclohexane-1,2-diamine in a solvent such as DMI to give compound 32. Step B shows the deprotection of compound 32 with methanesulfonic acid in a solvent such as ACN to give compound 33.
Scheme 7
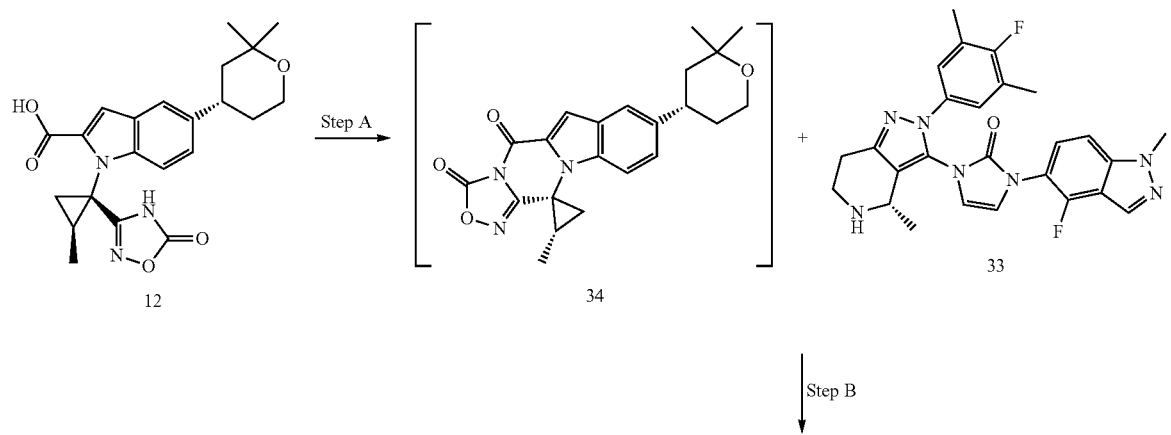

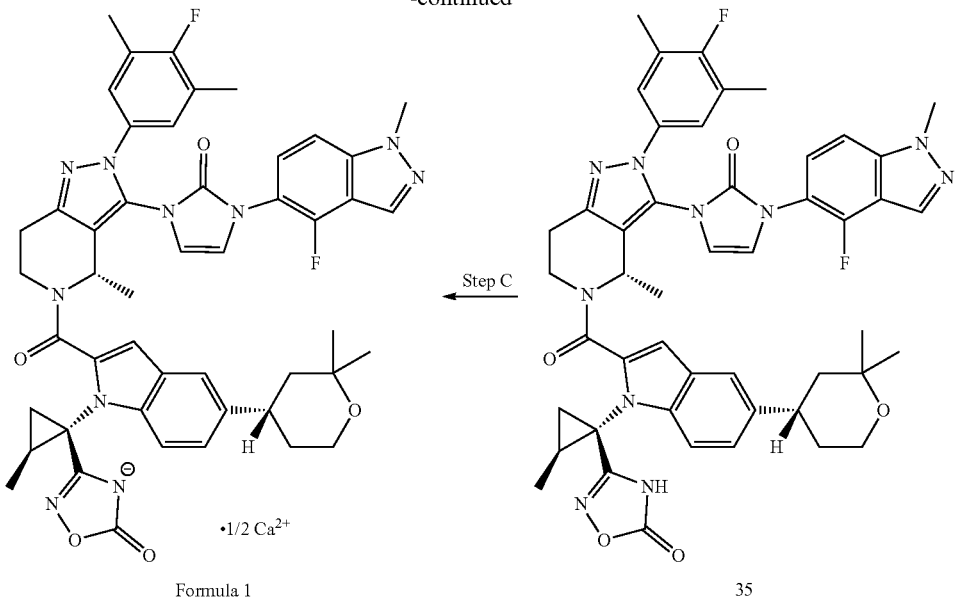

Formula I            35

Scheme 7, steps A and B show the formation of compound 34 when compound 12 is treated with coupling reagents such as HATU or COMU and a base such as DIPEA in solvents such as THF, DMI, and DMAc, followed by the amide coupling between compounds 34 and 33 to give compound 35. Step C shows the treatment of compound 35 with NaOH and calcium acetate dihydrate in a solvent system such as water and EtOH to give the compound of Formula I.

There are many possible solvent, base, and calcium salt combinations which could be used to carry out this reaction. In one embodiment, a suitable solvent was selected from methanol, isopropanol, tetrahydrofuran, acetonitrile, dimethylformamide, ethyl acetate, toluene, dichloromethane, dimethyl sulfoxide, tert-butyl methyl ether, dimethyl acetamide, and 1,4-dioxane. A suitable base was selected from sodium ethoxide, sodium tert-butoxide, potassium hydroxide, potassium ethoxide, potassium tert-butoxide, sodium tert-amylate, sodium hydride, and sodium bis(trimethylsilyl) amide. A suitable calcium salt was selected from calcium acetate, calcium citrate, calcium lactate, calcium gluconate, calcium chloride, calcium sulfate, calcium nitrate, calcium iodide, and tricalcium phosphate. This step could be carried out at a temperature ranging from 0 to 150° C. In one embodiment, the temperature was 0 to 50° C.

Preparation 1

5-Bromo-N-methyl-N-phenyl-1H-indole-2-carboxamide

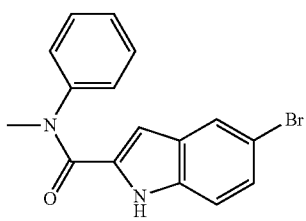 [SMILES: CN(C(=O)c1cc2cc(Br)ccc2[nH]1)c1ccccc1]

A reactor was charged with ACN (7951 kg), 5-bromo-1H-indole-2-carboxylic acid (991 kg, 4.13 kmol) and oxalyl chloride (654 kg, 5.15 kmol). A solution of DMF (151 kg, 2.07 kmol) in ACN (958 kg) was added dropwise at 20-30° C. and the mixture was stirred at 20-30° C. for 45 min. N-Methylaniline (550 kg, 5.13 kmol) was added at 0-20° C. and stirred for 2 h. TEA (1080 kg, 10.67 kmol) was added at 0-20° C. and stirred for 2 h. Water (1456 kg) was added, and the mixture was stirred at 20-30° C. for 2 h then filtered. The resulting wet cake was rinsed with ACN (2907 kg) and water (4845 kg) sequentially then dried under vacuum at 50-80° C. to a constant weight to give the title compound as a solid (1288.4 kg, 92%). mp (DSC): 259.2° C. $^1$H NMR (DMSO-$d_6$) δ 3.39 (br s, 3H), 5.27 (s, 1H), 7.23 (dd, J-8.78 Hz, 1.76 Hz, 1H), 7.34-7.52 (m, 7H), 11.81 (s, 1H). $^{13}$C NMR (DMSO-$d_6$) δ 38.91, 105.25, 112.48, 114.60, 123.99, 126.51, 128.08, 128.47, 128.87, 130.16, 131.89, 134.60, 144.48, 161.56. TOF-MS (ESI) m/z calculated: 328.0211, found: 329.0308 (M+H).

Alternative Preparation 1

A reactor was charged with 5-bromo-1H-indole-2-carboxylic acid (4.96 g, 20.66 mmol), DMF (0.81 mL, 10.5 mmol), and ACN (50 mL). A solution of oxalyl chloride (2.38 mL, 27.46 mmol) in ACN (10 mL) was added at a rate such that the temperature was maintained at <30° C. After the addition, the reaction was stirred vigorously for 60 min at ambient temperature. The temperature of the reaction was then adjusted to 5° C. and N-methylaniline (2.75 mL, 25.4 mmol) was added slowly while maintaining the internal temperature at <10° C. After 10 min of stirring, TEA (7.0 mL, 50 mmol) was slowly added to the mixture while maintaining the internal temperature at <30° C. The mixture was stirred for 2 h at ambient temperature and quenched with water (5 mL). The resulting slurry was stirred for 1 h at ambient temperature, filtered, and the resulting wet cake was washed with ACN (15 mL) and water (25 mL) sequentially. The wet cake was dried in vacuo at 70° C. for 24 h to give the title compound as a solid (6.50 g, 96%). Analytical data were consistent with those collected from Preparation 1.

Preparation 2

(E)-3-(2-(Methyl(phenyl) carbamoyl)-1H-indol-5-yl) acrylic acid

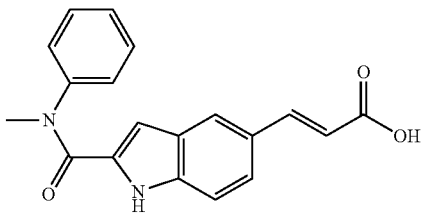 [SMILES: CN(C(=O)c1cc2cc(/C=C/C(=O)O)ccc2[nH]1)c1ccccc1]

A reactor was charged with 5-bromo-N-methyl-N-phenyl-1H-indole-2-carboxamide (60 kg, 182.3 mol) and N,N-dimethylacetamide (329 kg). The mixture was heated to 50-60° C. and purged with nitrogen. Tri-tert-butylphosphonium tetrafluoroborate (0.64 kg, 2.2 mol) and allylpalladium (II) chloride dimer (0.17 kg, 0.46 mol) were added under nitrogen atmosphere, and the mixture was purged with nitrogen. N,N-Dicyclohexylmethylamine (142 kg, 726.9 mol) and acrylic acid (19.4 kg, 273.4 mol) were added. The reaction was purged with nitrogen and stirred at 50-70° C. for 18 h. IM aqueous sulfuric acid (410 kg) was added at 50-70° C. to pH 3.68. Water (181 kg) was added, and the temperature was adjusted to 5-15° C. over 5 h. The mixture was stirred for 1-3 h, filtered, and the resulting wet cake was rinsed with water (420 kg) then dried under vacuum at 50-80° C. to a constant weight to give the title compound as a solid (52.7 kg, 87%). mp (DSC): 293.2° C. $^1$H NMR (DMSO-$d_6$) δ 3.39 (s, 3H), 5.31 (s, 1H), 6.36 (d, J=15.81 Hz, 1H), 7.38-7.62 (m, 9H). $^{13}$C NMR (DMSO-$d_6$) δ 38.91, 106.69, 113.18, 116.31, 123.35, 123.98, 126.70, 127.36, 128.18, 128.52, 130.21, 131.69, 137.04, 144.56, 145.86, 161.57, 168.36. TOF-MS (ESI) m/z calculated: 320.1161, found: 321.1260 (M+H).

Preparation 3

(R,E)-5-(3-(4-Benzyl-2-oxooxazolidin-3-yl)-3-oxo-prop-1-en-1-yl)-N-methyl-N-phenyl-1H-indole-2-carboxamide

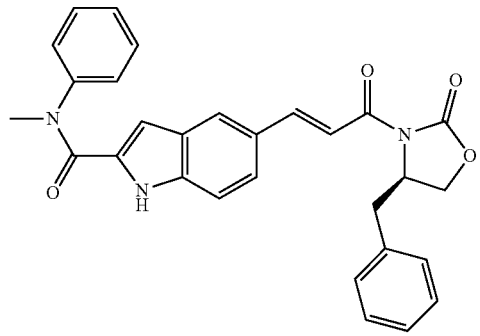 [SMILES: CN(C(=O)c1cc2cc(/C=C/C(=O)N3C(=O)OC[C@H]3Cc3ccccc3)ccc2[nH]1)c1ccccc1]

A reactor was charged with (E)-3-(2-(methyl(phenyl) carbamoyl)-1H-indol-5-yl) acrylic acid (585 kg, 1.83 kmol) and ACN (5646 kg). CDI (360 kg, 2.22 kmol) was added, followed by a rinse with ACN (342 kg). The reaction was stirred at 5-10° C. for 2 h, filtered, and the resulting wet cake was rinsed with ACN (3440 kg). The wet cake, N,N-dimethylacetamide (4002 kg), (R)-4-benzyl-2-oxazolidinone (401 kg, 2.26 kmol), and 1,8-diazabicyclo [5.4.0] undec-7-ene (718 kg, 4.72 kmol) were added to the reactor sequentially. The reaction was stirred at 10-25° C. for 1 h then quenched with 5N HCl (867.5 kg) to pH 4. The resulting suspension was stirred for 6-12 h and filtered. The wet cake was rinsed with water (2925 kg) and dried under vacuum at 50-80° C. to a constant weight to give the title compound as a solid (742 kg, 75%). mp (DSC): 236.6° C. 1H NMR (DMSO-$d_6$) δ 2.95-3.12 (m, 2H), 3.39 (s, 3H), 4.20 (dd, J=8.78 Hz, 2.76 Hz, 1H), 4.36 (t, J=8.41 Hz, 1H), 4.72-4.79 (m, 1H), 5.35 (s, 1H), 7.18-7.33 (m, 5H), 7.38-7.52 (m, 7H), 7.62-7.72 (m, 2H), 7.79-7.88 (m, 1H), 11.93 (s, 1H). $^{13}$C NMR (DMSO-$d_6$) δ 37.18, 38.89, 55.00, 66.52, 106.85, 113.47, 114.63, 123.16, 124.74, 126.81, 127.31, 127.47, 128.18, 128.56, 129.01, 129.93, 130.21, 131.93, 136.16, 137.33, 144.52, 146.98, 153.98, 161.53, 165.11. TOF-MS (ESI) m/z calculated: 479.1845, found: 480.1945 (M+H).

Preparation 4

5-((R)-1-((R)-4-Benzyl-2-oxooxazolidin-3-yl)-5-methyl-1-oxohex-5-en-3-yl)-N-methyl-N-phenyl-1H-indole-2-carboxamide

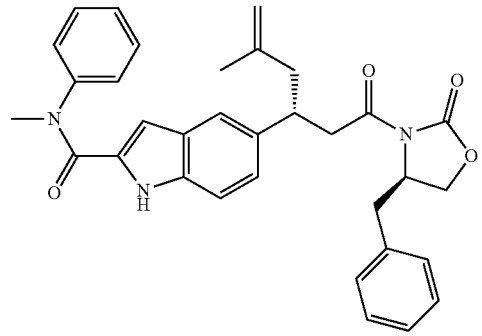 [SMILES: C=C(C)C[C@H](CC(=O)N1C(=O)OC[C@H]1Cc1ccccc1)c1ccc2[nH]c(C(=O)N(C)c3ccccc3)cc2c1]

A reactor was charged with 0.5M 2-methylallylmagnesium chloride in THF (1250 kg, 683 mol) and lithium chloride (30 kg, 707.6 mol). The mixture was stirred at 10-25° C. for 30-90 min and cooled to between −80 and −40° C. Copper (I) iodide (134 kg, 703.6 mol) was added at <−30° C., followed by a rinse with THF (94 kg). The reaction was stirred at between −50 and −30° C. for 10 min, and (R,E)-5-(3-(4-benzyl-2-oxooxazolidin-3-yl)-3-oxoprop-1-en-1-yl)-N-methyl-N-phenyl-1H-indole-2-carboxamide (95 kg, 198 mol) was added at <−30° C., followed by a rinse with THF (143 kg). The reaction was stirred between −40 and −20° C. for 4 h then quenched with 10% aqueous ammonium chloride solution (500 kg) at <0° C. MTBE (232 kg) was added, and the layers were separated. Ethylenediamine (31 kg) was added to the organic layer, and the mixture was stirred at 20-30° C. for 1-3 h. 10% Aqueous ammonium chloride solution (398 kg) was added, and the mixture was stirred at 20-30° C. for 30-60 min. The layers were separated, and the organic phase was filtered through a pad of diatomaceous earth. The pad was rinsed with THF (95 kg), and the combined filtrates were washed with 1% aqueous acetic acid solution (315 kg) and 10% aqueous ammonium chloride solution (408 kg) sequentially. The organics were concentrated to 3-5 vol and solvent swapped to ~39 vol of EtOH under reduced pressure at <50° C. The resulting mixture was heated at ~80° C. until a clear solution was resulted, after which the mixture was cooled to 5-10° C. at a rate of 10° C./h. The resulting suspension was stirred at 5-10° C. for 1-3 h and filtered. The filter cake was added back to the reactor with EtOH (2634 kg). The mixture was heated at 78° C. until a clear solution resulted, after which the mixture was cooled to 5-10° C. at a rate of 10° C./h. The resulting suspension was stirred at 5-10° C. for 1-3 h and filtered. The filter cake was dried under vacuum at 55-80° C. to a constant weight to give the title compound as a solid (81.54 kg, 77%). mp (DSC): 158.3° C. $^1$H NMR (DMSO-$d_6$) δ 1.61 (s, 3H), 2.25-2.42 (m, 2H), 2.74-2.89 (m, 2H), 2.99-3.19 (m, 2H), 3.35-3.45 (m,4 H), 4.05-4.14 (m, 2H), 4.42-4.48 (m, 1H), 4.58 (br d, J=16.56 Hz, 2H), 5.17 (s, 1H), 7.05 (d, J=8.53 Hz, 1H), 7.10-7.15 (m, 3H), 7.22-7.48 (m, 9H), 11.46 (s, 1H). $^{13}$C NMR (DMSO-$d_6$) δ 22.45, 37.07, 38.89, 40.62, 42.30, 45.07, 54.65, 66.42, 105.88, 112.31, 112.87, 120.23, 124.23, 127.17, 127.28, 128.25, 128.43, 128.97, 129.81, 130.15, 130.57, 134.92, 135.70, 136.14, 143.81, 144.74, 153.67, 161.86, 171.69. TOF-MS (ESI) m/z calculated: 535.2471, found: 536.2572 (M+H).

Alternative Preparation 4

A reactor was charged with 0.5M 2-methylallylmagnesium chloride in THF (1320 kg, 721 mol) and lithium chloride (31 kg, 731.3 mol). The mixture was cooled to −42° C., after which copper (I) iodide (140 kg. 735.1 mol) and (R,E)-5-(3-(4-benzyl-2-oxooxazolidin-3-yl)-3-oxoprop-1-en-1-yl)-N-methyl-N-phenyl-1H-indole-2-carboxamide (100 kg, 208.5 mol) were added at <−30° C. The reaction was stirred between −40 and −20° C. for 8 h then quenched with 10% aqueous ammonium chloride solution (480 kg). MTBE (220 kg) was added, the content was stirred for 1 h, and the layers were separated. Ethylenediamine (63 kg) was added to the organic layer and the mixture was stirred at 20-30° C. for 2 h. 10% Aqueous ammonium chloride solution (400 kg) was added, and the mixture was stirred at 20-30° C. for 30-60 min. The layers were separated, and the organic phase was filtered through a pad of diatomaceous earth. The pad was rinsed with THF (89 kg), and the combined filtrates were washed with 10% aqueous ammonium chloride solution (300 kg). The organic phase was concentrated in vacuo, and solvent swapped with EtOH (948 kg) to 5 vol under reduced pressure at <50° C. EtOH (2370 kg) was added and the resulting mixture was heated at 80° C. until a clear solution resulted, after which the mixture was cooled to 5-10° C. over 3 h. The resulting suspension was filtered, and the filter cake was rinsed with EtOH (100 kg). The solid was dried under vacuum at 50-80° C. to a constant weight to give the title compound as a solid (85.8 kg, 76%). Analytical data were consistent with those collected from Preparation 4.

Alternative Preparation 4-CSTR Process

Feeds Preparations

Pump A feed: A dry 3000-L glass-lined reactor (FLR1) was charged with 0.5M 2-methylallylmagnesium chloride THF solution (1381.3 kg, 750.7 mol) and LiCl (31.8 kg, 750.7 mol) at 10-30° C. and stirred for 0.5-1 h as Material A.

Pump B feed: CuI (3 kg, 15.75 mol) in THF (6 L) in a 50 L stirring tank (FLR5) was used as Material B(Prepare every ~40 min, total CuI: 143.0 kg, 750.1 mol).

Starting material mixture: A dry 5000-L stainless steel reactor (FLR4) was charged with (R,E)-5-(3-(4-benzyl-2-oxooxazolidin-3-yl)-3-oxoprop-1-en-1-yl)-N-methyl-N-phenyl-1H-indole-2-carboxamide (150 kg, 312.8 mol), and THF (1201.5 kg) at −45° C.--35° C. The reaction mixture was stirred as Material C.

Quenching solution: A dry 5000-L stainless steel reactor (FLR6) was charged with citric acid monohydrate (79.5 kg, 378.3 mol) and water (750 kg, 5.0 vol) at 15-30° C. The solution was stirred for 0.5-1 h.

Configuration of pumps and CSTRs: Pump 1 was connected from Material A reactor (FLR1) to CSTR1 (FLR2, 100 L). Pump 2 was connected from CuI/THF stirring tank (FLR5) to CSTR1 (FLR2), then CSTR1 (FLR2, 100 L, Cu complex), CSTR2 (FLR3, 100L, Cu complex), reaction reactor (FLR4) and quench reactor (FLR6) were connected. The flow rate of pump 1 was set by automatic control system as 800 mL/min. (Residence time in FLR2:87.5 min, Residence time in FLR3:37.5 min).

CSTR system preparation: Agitation was initiated in FLR2 and FLR3. THF (150 kg) was pumped through all CSTR stages, after which pumps were stopped and THF in CSTR 4 was analyzed for residual water by KF until KF was ≤500 ppm. The two CSTRs (FLR2 and FLR3) were cooled to −45° C.--20° C.

CSTR system startup and shutdown: Pump 1 was started to pump material A solutions to CSTR 1 (FLR2). After ~40 min, pumped material B into CSTR1 then pumped material B around every 40 min. The copper complex mixture after CSTR 2 was transferred to 5000-L stainless steel reactor (FLR4) containing (R,E)-5-(3-(4-benzyl-2-oxooxazolidin-3-yl)-3-oxoprop-1-en-1-yl)-N-methyl-N-phenyl-1H-indole-2-carboxamide/THF with stirring at −45° C.--35° C. The reaction was monitored by HPLC analysis at the reaction reactor (FLR4) for the conversion of (R,E)-5-(3-(4-benzyl-2-oxooxazolidin-3-yl)-3-oxoprop-1-en-1-yl)-N-methyl-N-phenyl-1H-indole-2-carboxamide (IPC specs: ≤1.0% of (R,E)-5-(3-(4-benzyl-2-oxooxazolidin-3-yl)-3-oxoprop-1-en-1-yl)-N-methyl-N-phenyl-1H-indole-2-carboxamide). Then, the reaction mixture in FLR4 was transferred to FLR6 for quenching at −10~25° C.

Work-up and isolation: The quenched mixture was diluted with MTBE (600 L, 4 vol). The layers were separated, and the organic layer was washed with 10% NH$_4$Cl aqueous solution (750 L, 5 vol). Ethylenediamine (94.5 kg, 1.57 kmol) was added to the mixture and agitated at ambient temperature for 1 h. The mixture was washed with 10% NH$_4$Cl aqueous solution (750 L, 5 vol) 3 times and then with 5% Na$_2$SO$_4$ aqueous solution (750 L, 5 vol). The mixture was solvent swapped to EtOH (3000 L, 20 vol), and the resulting mixture was heated to 80° C. and stirred for 2 h. The batch temperature was adjusted to 5° C. over 3 h, and further stirred for 3 h. The resulting suspension was filtered, and the filter cake was rinsed with EtOH (600 L, 4 vol). The solid was dried under vacuum at 70° C. to give the title product as a solid (130 kg, 80%). Analytical data were consistent with those collected from Preparation 4.

Preparation 5

(R,E)-N-Methyl-5-(3-oxo-3-(2-oxo-4-phenyloxazolidin-3-yl) prop-1-en-1-yl)-N-phenyl-1H-indole-2-carboxamide

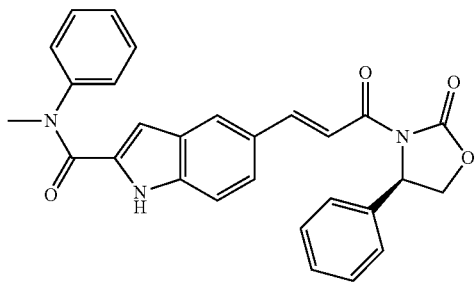 [SMILES: CN(C(=O)c1cc2cc(/C=C/C(=O)N3C(=O)OC[C@H]3c3ccccc3)ccc2[nH]1)c1ccccc1]

A reactor was charged with (E)-3-(2-(methyl(phenyl)carbamoyl)-1H-indol-5-yl) acrylic acid (20 g, 62.4 mmol) and DMAc (140 mL), and the contents were stirred for 20 min to form a clear solution. The internal temperature was cooled to 5° C., and CDI (11.7 g, 72.2 mmol) was added. The reaction was stirred for 2-4 h, after which (R)-4-phenyloxazolidin-2-one (17.7 g, 109.4) and DBU (27.5 g, 180.6 mmol) were added, followed by a rinse with DMAc (20 mL). The reaction was stirred at 20° C. for 4 h and quenched with 5N HCl (70 mL) at ≤40° C. to adjust pH to 3-5. The resulting suspension was cooled to 0° C. and further stirred for 12 h. The suspension was filtered, and the solids were slurried in a mixture of DMAc (140 mL) and water (60 mL). The suspension was filtered, and the solids were dried under vacuum at 60° C. for 16 h to a constant weight to give the title compound as a solid (25 g, 80%). $^1$H NMR (DMSO-$d_6$) δ 11.94 (s, 1H), 7.79-7.65 (m, 2H), 7.62 (s, 1H), 7.51-7.24 (m, 12H), 7.58 (dd, J=8.5, 3.75 Hz, 1 H), 5.35 (s, 1H), 4.79 (t, J-8.63 Hz, 1H), 4.19 (dd, J-8.5, 3.75 Hz, 1H), 3.4 (s, 3H). 13C NMR (DMSO-$d_6$) ô 164.6, 161.5, 154.4, 147.1, 144.5, 140.4, 137.4, 131.9, 130.2, 129.3, 128.6, 128.4, 128.2, 127.5, 126.8, 126.3, 124.9, 123.1, 114.7, 113.5, 106.9, 70.6, 57.7, 38.9. TOF-MS (ESI) m/z calculated: 466.1761, found: 466.1774 (M+H).

Preparation 6

(R)-5-(1-Hydroxy-5-methylhex-5-en-3-yl)-N-methyl-N-phenyl-1H-indole-2-carboxamide

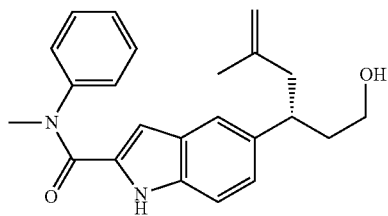 [SMILES: C=C(C)C[C@H](CCO)c1ccc2[nH]c(C(=O)N(C)c3ccccc3)cc2c1]

A reactor was charged with 5-((R)-1-((R)-4-benzyl-2-oxooxazolidin-3-yl)-5-methyl-1-oxohex-5-en-3-yl)-N-methyl-N-phenyl-1H-indole-2-carboxamide (525 kg, 0.98 kmol) and THF (2658 L). The reaction temperature was adjusted to 20-30° C. and the mixture was stirred until a clear solution resulted. Glacial acetic acid (5.4 kg, 89.9 mol), water (10 kg, 555.6 mol), and EtOH (154 kg, 3.34 kmol) were added. The mixture was cooled to -20° C., and 2M lithium borohydride solution in THF (450 kg, 1 kmol) was added at <-5° C., then stirred at 0-10° C. for 15 h. The reaction was quenched with 10% aqueous ammonium chloride solution (2603 L) at <10° C. The mixture was diluted with MTBE (1056 L) and the aqueous layer was removed, and the organic layer was washed with water (1570 L). The organic phase was concentrated in vacuo and solvent swapped twice with MeOH (5498 L) to ~10 vol under reduced pressure at <50° C. The resulting mixture was heated at 65° C. until a clear solution was obtained, after which the mixture was cooled to 5-10° C. over 5 h and filtered. The filter cake was rinsed with water (525 L) and dried under vacuum at 50-80° C. to a constant weight to give the title compound as a solid (279 kg, 74%). mp (DSC): 180.5° C. $^1$H NMR (DMSO-$d_6$) δ 1.40-1.62 (m, 4H), 1.64-1.82 (m, 1H), 2.14-2.33, (m, 2H), 2.75-2.95 (m, 1H), 3.04-3.22 (m, 2H), 3.38 (s, 3 H), 4.25 (t, J=5.14 Hz, 1H), 4.53 (br d, J=12.30 Hz, 2H), 5.15-5.20 (m, 1H), 7.00 (d, J-8.54 Hz, 1H), 7.05 (s, 1H), 7.27-7.34 (m, 1H), 7.36-7.52 (m, 5H), 11.46 (s, 1H). 13C NMR (DMSO-$d_6$) δ 22.53, 38.91, 39.84, 40.61, 45.74, 59.29, 105.82, 112.30, 120.14, 124.07, 127.24, 128.29, 128.43, 130.18, 130.43, 134.82, 136.68, 144.27, 144.77, 161.89. TOF-MS (ESI) m/z calculated: 362.1994, found: 363.2091 (M+H).

Alternative Preparation 6

To a 12500-L reactor was charged 5-((R)-1-((R)-4-benzyl-2-oxooxazolidin-3-yl)-5-methyl-1-oxohex-5-en-3-yl)-N-methyl-N-phenyl-1H-indole-2-carboxamide (550 kg, 1.03 kmol) and EtOH (5500 L). The internal temperature was adjusted to -15° C. and MgCl$_2$ (100 kg, 1.05 kmol) was charged into the reactor at -15° C. A lithium borohydride solution in THF (636 kg, 1.41 kmol) was charged at -15° C., and the reaction was stirred at -15° C. for 20 h, at which point HPLC analysis indicated consumption of the starting material [5-((R)-1-((R)-4-benzyl-2-oxooxazolidin-3-yl)-5-methyl-1-oxohex-5-en-3-yl)-N-methyl-N-phenyl-1H-indole-2-carboxamide: <0.5%]. The reaction was quenched with 10% NH$_4$Cl aqueous solution (2716 L, 5 vol), and the mixture was concentrated to 4 vol at <50° C. The mixture was extracted with 2-MeTHF (4128 L, 7.5 vol), and the organic layer was washed with water (2756 L, 5 vol). The organic phase was concentrated to about 1.5 vol and MeOH (2758 L, 5 vol) was charged. The content was concentrated under reduced pressure (-0.09-0.1 MPa) at <65° C. to 1.5 vol and MeOH (2763 L, 5 vol) was charged. The content was concentrated under reduced pressure (-0.09-0.1 MPa) at <65° C. to 1.5 vol and MeOH (4408 L, 8 vol) and water (1728 L, 3 vol) were added sequentially, and the mixture was heated to 65° C. The mixture was stirred for 2 h and cooled to 55° C. over 1 h. Seeds (2.76 kg, 0.5 wt %) were added and the resulting suspension was cooled to 5° C. over 5 h, stirred for 8 h, and filtered. The resulting wet cake was rinsed with water (1650 L, 3 vol) and dried under vacuum at 65° C. to a constant weight to give the title compound as a solid (297 kg, 77%). Analytical data were consistent with those collected from Preparation 6.

Preparation 7

N-Methyl-5-((R)-5-methyl-1-oxo-1-((R)-2-oxo-4-phenyloxazolidin-3-yl) hex-5-en-3-yl)-N-phenyl-1H-indole-2-carboxamide

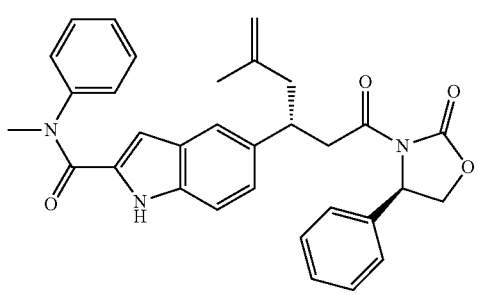 [SMILES: C=C(C)C[C@H](CC(=O)N1C(=O)OC[C@H]1c1ccccc1)c1ccc2[nH]c(C(=O)N(C)c3ccccc3)cc2c1]

A reactor was charged with (2-methylallyl) magnesium chloride (0.5M solution in THF, 1381 g, 754.6 mmol) and LiCl (31.8 g, 750.1 mmol). The mixture was adjusted to 25° C. and stirred for 30 min. The mixture was cooled to −45° C., and CuI (143.2 g, 751.9) was added while maintaining the temperature at <-40° C. The reaction was further stirred at −45° C. for 30 min, after which (R,E)-N-methyl-5-(3-oxo-3-(2-oxo-4-phenyloxazolidin-3-yl) prop-1-en-1-yl)-N-phenyl-1H-indole-2-carboxamide (100 g, 214.8 mmol) was added. The reaction was adjusted to −35° C. and stirred for 4.5 h at −35° C. Aqueous citric acid (0.5N, 500 mL) was charged at <0° C. over 1 h. The mixture was diluted with MTBE (300 mL) and the layers were separated. The aqueous layer was extracted with THF (500 mL) and the combined organics were washed with 10% aqueous NH$_4$Cl (500 mL). The organics were treated with ethane-1,2-diamine (65 g, 1.08 mol) for 2 h at 25° C. and washed with 10% aqueous NH$_4$Cl (500 mL×2). The organics were concentrated to 1-2 vol and solvent exchanged to methyl ethyl ketone (600 mL). The resulting mixture was heated to 75° C. to afford a clear solution, which was cooled to 65° C. and seeded. The resulting suspension was stirred for an additional 2 h at 65° C., after which n-heptane (600 mL) was added at 65° C. over 1.5 h. The slurry was cooled to 25° C. over 2.5 h and further stirred for 8 h. The suspension was filtered, and the filter cake was rinsed with n-heptane (200 mL) and dried under vacuum at 60° C. for 16 h to a constant weight to give the title compound as a solid (84 g, 80%). $^1$H NMR (CDCl$_3$) δ 9.40 (s, 1H), 7.44-7.42 (m, 3H), 7.28-7.24 (m, 2H), 7.21-7.19 (m, 4H), 7.10-7.07 (m, 3H), 7.02 (dd, J=8.5, 1.63 Hz, 1H), 5.10-5.06 (m, 2H), 4.52 (d, J=11.6 Hz, 2H), 4.29 (t, J=8.7 Hz, 1H), 4.05 (dd, J-8.8, 3.4 Hz, 1H), 3.43 (s, 3H), 3.35-3.31 (m, 1H), 3.03-3.00 (d, J=12.3 Hz, 1H), 2.23-2.21 (d, J=7.0 Hz, 2H), 1.51 (s, 3H). $^{13}$C NMR (CDCl$_3$) δ 171.54, 161.98, 153.68, 144.09, 143.29, 138.99, 135.83, 134.27, 130.02, 129.75, 129.04, 128.61, 128.55, 128.04, 127.74, 125.85, 124.71, 120.69, 112.79, 111.45, 107.06, 69.80, 57.50, 45.68, 41.56, 39.33, 38.98, 22.16. TOF-MS (ESI) m/z calculated: 522.2415, found: 522.2387 (M+H).

Preparation 8

(S)-5-(2,2-Dimethyltetrahydro-2H-pyran-4-yl)-N-methyl-N-phenyl-1H-indole-2-carboxamide

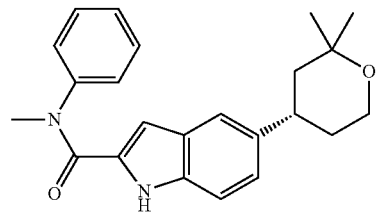 [SMILES: CN(C(=O)c1cc2cc([C@H]3CCOC(C)(C)C3)ccc2[nH]1)c1ccccc1]

A reactor was charged with (R)-5-(1-hydroxy-5-methyl-hex-5-en-3-yl)-N-methyl-N-phenyl-1H-indole-2-carboxamide (147 kg, 405.6 mol), p-toluenesulfonic acid monohydrate (190 kg, 1.0 kmol) and cyclopentyl methyl ether (600 kg). The reaction was heated at 60-70° C. for 12 h, and then quenched with 1N aqueous sodium hydroxide solution (1072 L). IPA (147 kg) and n-heptane (1080 L) were added sequentially, and the mixture was cooled to 5-10° C. at a rate of 10° C./h. The resulting suspension was filtered, and the filter cake was rinsed with IPA (147 kg). The wet cake was slurried in a mixture of water (1892 kg) and IPA (218 kg) at 60-70° C. for 1 h and cooled to 20-30° C. The resulting suspension was stirred at 20-30° C. for 2 h and filtered. The filter cake was dried under vacuum at 50-80° C. to a constant weight to give the title compound as a solid (128.4 kg, 87%). mp (DSC): 220.1° C. $^1$H NMR (DMSO-d$_6$) δ 0.75-1.75 (m, 12H), 2.72-2.99 (m, 1H), 3.54-3.70 (m, 3H), 5.21 (br s, 1H), 7.04 (s, 1H), 7.09 (s, 1H), 7.21-7.41 (m, 3H), 7.46 (br s, 3H) 11.48 (br s, 1H). $^{13}$C NMR (DMSO-d$_6$) δ 22.03, 31.99, 34.09, 36.94, 38.82, 44.86, 61.24, 71.65, 105.90, 112.41, 118.77, 123.81, 127.28, 128.17, 128.31, 130.08, 130.56, 134.78, 137.85, 144.75, 161.94. TOF-MS (ESI) m/z calculated: 362.1994, found: 363.2098 (M+H).

Alternative preparation 8

(R)-5-(1-Hydroxy-5-methylhex-5-en-3-yl)-N-methyl-N-phenyl-1H-indole-2-carboxamide

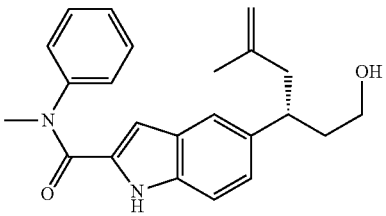 [SMILES: C=C(C)C[C@H](CCO)c1ccc2[nH]c(C(=O)N(C)c3ccccc3)cc2c1]

A reactor was charged with N-methyl-5-((R)-5-methyl-1-oxo-1-((R)-2-oxo-4-phenyloxazolidin-3-yl) hex-5-en-3-yl)-N-phenyl-1H-indole-2-carboxamide (20 g, 38.4 mmol), EtOH (160 mL), THF (40 mL), and MgCl$_2$ (1.85 g, 19.4 mmol). The mixture was cooled to −15° C., and a 2N solution of LiBH$_4$ in THF (19 mL, 38.0 mmol) was added at −15° C. The reaction was stirred for 16 h and then quenched with 10% aqueous NH$_4$Cl (100 mL) at <0° C. The mixture was warmed to 10-20° C. and concentrated to 5-7 vol. The remaining mixture was extracted with 2-MeTHF (200 mL×2). The organic layers were combined and washed with water (100 mL). The solvent of the organics was swapped to MeOH (800 mL) and diluted with water (200 mL). The mixture was heated to 60° C. to give a clear solution, which was cooled to 20° C. over 2 h. The resulting suspension was further stirred for 16 h and filtered. The filter cake was rinsed with water (100 mL) and dried under vacuum at 60° C. for 16 h to a constant weight to give the title compound as a solid (10 g, 70%). Analytical data were consistent with those collected from Preparation 8.

Preparation 9

(S)-1-(Cyanomethyl)-5-(2,2-dimethyltetrahydro-2H-pyran-4-yl)-N-methyl-N-phenyl-1H-indole-2-carboxamide

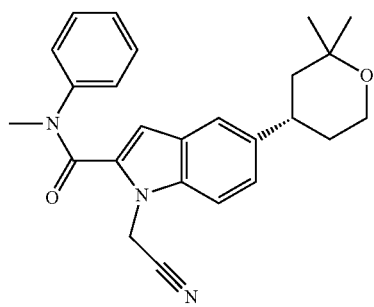 [SMILES: CN(C(=O)c1cc2cc([C@H]3CCOC(C)(C)C3)ccc2n1CC#N)c1ccccc1]

A reactor was charged with(S)-5-(2,2-dimethyltetrahydro-2H-pyran-4-yl)-N-methyl-N-phenyl-1H-indole-2-carboxamide (100 g, 0.27 mol) and toluene (1200 mL). The mixture was heated at 50° C. for 2 h and cooled to ambient temperature. Potassium hydroxide (50 wt %, 61.93 g, 1.1 mol) and tetrabutylammonium chloride hydrate (7.35 g, 0.025 mol) were added and the mixture was cooled to 0° C. A solution of chloroacetonitrile (26.04 g, 0.345 mol) in toluene (200 mL) was added slowly with vigorous agitation and the reaction was further stirred for 2 h after addition. The aqueous layer was separated, and the organic layer was washed with 5% aqueous sodium bicarbonate solution (300 mL×5). The organic layer was treated with activated charcoal, filtered, and crystallized from a mixture of MTBE (100 mL) and n-heptane (1100 mL). The resulting suspension was filtered, and the filter cake was dried under vacuum at 50° C. to give the title compound (100 g, 90%). mp (DSC): 84.3° C. $^1$H NMR (CDCl$_3$) δ 1.28 (d, J=19.6 Hz, 6H), 1.54-1.72 (m, 4H), 2.91-2.95 (m, 1H), 3.53 (s, 2H), 3.75-3.86 (m, 2H), 5.55 (s, 2H), 5.91 (s, 1H), 7.17-7.47 (m, 8H). $^{13}$C NMR (CDCl$_3$) δ 21.76, 31.73, 32.44, 33.83, 37.39, 38.52, 44.73, 61.79, 71.88, 109.15, 110.76, 115.48, 119.86, 124.88, 126.61, 127.01, 127.60, 129.70, 130.18, 135.97, 139.41, 144.64, 162.58. TOF-MS (ESI) m/z calculated: 402.2176, found: 402.2249 (M+H).

Preparation 10

1-((1S,2S)-1-Cyano-2-methylcyclopropyl)-5-((S)-2,2-dimethyltetrahydro-2H-pyran-4-yl)-N-methyl-N-phenyl-1H-indole-2-carboxamide

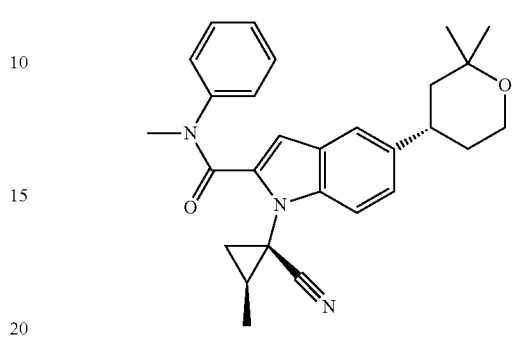

(S)-1-(Cyanomethyl)-5-(2,2-dimethyltetrahydro-2H-pyran-4-yl)-N-methyl-N-phenyl-1H-indole-2-carboxamide (100 g, 0.24 mol) was dissolved in DMF (633 g) and labeled as Solution 1. (R)-4-Methyl-1,3,2-dioxathiolane 2,2-dioxide (110 g, 0.77 mol) was dissolved in THF (200 mL) and labeled as Solution 2.

A CSTR with four reactors, namely Reactor A, Reactor B, Reactor C, and Reactor D, was set up. Solution 1 (5.73 mL/min), Solution 2 (1.71 mL/min), and a 1.0M solution of potassium bis(trimethylsilyl)amide in THF (6.04 mL/min) were pumped into Reactor A at the indicated flow rates simultaneously while maintaining the internal temperature at −10° C. The reaction mixture in Reactor A (residence time: 2 min) was continually pumped into Reactor B. The reaction mixture in Rector B (residence time: 2 min) was then pumped into Reactor C at the same flow rate, and the mixture in Reactor C (residence time: 2 min) was pumped into Reactor D at the same flow rate. After the reaction, the mixture was pumped into a container and quenched with 50% aqueous acetic acid solution to pH 5-7 (residence time: 17 min). The quenched mixture was concentrated to remove THF and diluted with ACN (200 mL). Water (330 mL) was added at ambient temperature to precipitate the crude product, and the filter cake was crystallized from a mixture of ACN (400 mL) and water (400 mL). The wet cake was dissolved in ACN (400 mL) at 45° C. and filtered to remove sticky material, and water (400 mL) was slowly added to the filtrate. The resulting suspension was slowly cooled to ambient temperature and filtered. The filter cake was dried under vacuum at 50° C. to give the title compound (71 g, 65%). mp (DSC): 180.9° C. $^1$H NMR (CDCl$_3$) δ 1.29 (d, J=19.6 Hz, 6H), 1.76-1.53 (m, 10H), 1.94-1.80 (m, 2H), 3.01-2.89 (m, 1H), 3.54 (s, 3 H), 3.88-3.75 (m, 2H), 5.89 (s, 1H), 7.45-7.10 (m, 8H). $^{13}$C NMR (CDCl$_3$) δ 15.45, 21.77, 24.89, 31.35, 31.75, 33.87, 37.39, 38.40, 44.79, 61.81, 71.89, 109.81, 110.61, 118.28, 119.77, 124.35, 126.59, 126.76, 127.37, 129.57, 132.00, 136.29, 139.34, 144.51, 162.00. TOF-MS (ESI) m/z calculated: 442.2489, found: 442.2526 (M+H).

Alternative Preparation 10

A reactor was charged with(S)-1-(cyanomethyl)-5-(2,2-dimethyltetrahydro-2H-pyran-4-yl)-N-methyl-N-phenyl-1H-indole-2-carboxamide (100 g, 0.24 mol), (R)-4-methyl-1,3,2-dioxathiolane 2,2-dioxide (68.8 g, 0.49 mol), and THF (500 mL) at 0° C. A 2N solution of lithium t-butoxide in THF (805 g, 1.92 mol) was added slowly, and the reaction was stirred for an additional 20 h. The mixture was quenched with 50% aqueous acetic acid solution (240 g) and diluted with n-heptane (500 mL). The layers were separated, and the organic layer was washed with water (2× 500 mL). The organic layer was solvent swapped to ACN (500 mL) and water (420 mL) was added. The suspension was filtered and the solid was recrystallized from a mixture of ACN (400 mL) and water (330 mL). The suspension was filtered, and the filter cake was dried in vacuum at 50° C. to give the title compound as a solid (78 g, 71%). Analytical data were consistent with those collected from Preparation 10.

Alternative Preparation 10

A reactor was charged with(S)-5-(2,2-dimethyltetrahydro-2H-pyran-4-yl)-N-methyl-N-phenyl-1H-indole-2-carboxamide (100 g, 275.9 mmol) and toluene (1200 mL). Potassium hydroxide (50 wt %, 123.85 g, 1.1 mol) and tetrabutylammonium chloride hydrate (7.35 g, 24.8 mmol) were added and the mixture was cooled to 0° C. A solution of chloroacetonitrile (26 g, 344 mmol) in toluene (200 mL) was added slowly and the reaction was further stirred for 1 h after addition. 5 wt % Aqueous sodium bicarbonate solution (300 mL) was charged at 0° C. The mixture was warmed to 20° C. and stirred for 30 min. The layers were separated, and the organic layer was washed with 5 wt % aqueous sodium bicarbonate solution (300 mL×5). Toluene (500 mL) was added to the organic layer, and the resulting organics were filtered through a diatomaceous earth pad. The pad was rinsed with toluene (300 mL) and filtrates were allowed to stand and separated to remove any aqueous layer. The organic layer was cycled through CUNO and the CUNO pad was rinsed with toluene (300 mL). The combined filtrates were azeotropically distilled with toluene to 2 vol until KF≤0.1%. THF (800 mL) was added, and the mixture was cooled to 0° C. (R)-4-Methyl-1,3,2-dioxathiolane 2,2-dioxide (68.81 g, 498 mmol) was added at 0° C., and the resulting mixture was stirred at 0° C. for 20 min. Lithium t-butoxide (152.39 g, 1.9 mol) was added slowly, and the mixture was stirred for 19 h. The mixture was quenched with 50% aqueous acetic acid solution (239 g) then diluted with n-heptane (500 mL) and water (500 mL). The layers were separated, and the organic layer was washed with water (500 mL). The organic layer was concentrated to ~200 mL and solvent swapped to ACN (500 mL). The mixture was heated to 50° C., and water (167 mL) was added. The resulting suspension was stirred at 50° C. for 1.5 h, cooled to 20° C. over 4 h, and stirred for 13 h at 20° C. Water (280 mL) was added over 3 h, and the suspension was stirred at 20° C. for 16 h. The suspension was filtered, and the solid was recrystallized from a mixture of ACN (500 mL) and water (340 mL) to give the title compound as a solid after drying to constant weight under vacuum at 55° C. (75.65 g, 62%). Analytical data were consistent with those collected from Preparation 10.

Preparation 11

(S)-2-((tert-Butoxy carbonyl)amino) propyl methanesulfonate

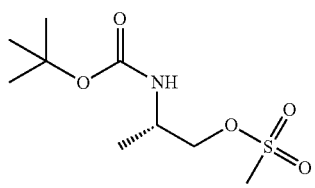 [SMILES: C[C@@H](COS(C)(=O)=O)NC(=O)OC(C)(C)C]

A vessel was charged with tert-butyl(S)-(1-hydroxypropan-2-yl) carbamate, (200 g. 1.14 mol) and DCM (400 mL). The mixture was cooled to 0-5° C. TEA (173.24 g, 1.71 mol) was added over 20 min while keeping the internal temperature below 10° C. A solution of methane sulfonic anhydride (218.71 g, 1.26 mol) dissolved in DCM (600 mL) was added over 4 hours to the reaction while keeping the internal temperature below 5° C. The reaction contents were stirred for another 30 min at this temperature. Upon reaction completion (about 30 min), water (400 mL) was added over 30 min while maintaining the internal temperature below 8° C. The aqueous phase was separated and further extracted with DCM (800 mL). The organic phases were combined and washed with 10% aqueous citric acid (800 mL), 8% NaHCO₃ (800 mL), and 10% aqueous NaCl (800 mL) successively. The organic layer was concentrated in vacuo to ~400 mL and n-heptane (400 mL) was added. The suspension was cooled to 0-10° C. and stirred for 2 h. The resulting mixture was filtered and dried to give the title compound as a solid (290 g, 99+%). ¹H NMR (CDCl₃) δ 4.74-4.62 (m, 1H), 4.25 (d, J=9.9 Hz, 1H), 4.16 (ddd, J=10.1, 4.2, 2.0 Hz, 1H), 3.99 (s, 1H), 3.05 (q, J=1.8 Hz, 3H), 1.46 (s, 9H), 1.25 (d, J=7.1 Hz, 3H).

Preparation 12 tert-Butyl(S)-(1-cyanopropan-2-yl) carbamate

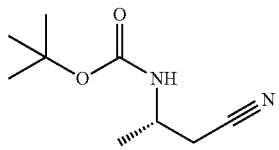

A vessel was charged with DMF (1.2 L), NaCN (75.45 g, 1.54 mol) and TBAB (38.178 g, 0.118 mol). The mixture was heated to 35-45° C. then(S)-2-((tert-butoxycarbonyl) amino) propyl methanesulfonate (300 g, 1.184 mol) dissolved in DMF (300 mL) was added, followed by stirring for 18 h. The mixture was cooled to 15-25° C. and water (4.5 L) and MTBE (6 L) were added. The aqueous phase was separated and further extracted with MTBE (6 L). The organic phases were combined and washed with water (1.8 L×3) then once with saturated aqueous sodium chloride (1.8 L). The organic layer was concentrated in vacuo to about 300 mL, and MTBE (900 mL) was added. The organic layer was concentrated in vacuo to about 300 mL and n-heptane (1.2 L) was added. The resulting mixture was filtered and dried to give the title product as a solid (160 g, 73.3%). ¹H NMR (CDCl₃) δ 4.65 (s, 1H), 3.95 (s, 1H), 2.80-2.69 (m, 1H), 2.56-2.49 (m, 1H), 1.44 (d, J=3.3 Hz, 9H), 1.32 (dd, J=6.7, 3.0 Hz, 3H).

Preparation 13

(S)-3-Aminobutanenitrile hydrochloride

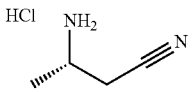

A vessel was charged with tert-butyl(S)-(1-cyanopropan-2-yl) carbamate (235 g, 1.276 mol) and DCM (1.88 L). HCl gas was added (139.67 g, 3.827 mol) while keeping reaction temp at 15-25° C. The contents were stirred for 6 h, then the mixture was cooled to 0-5° C. and stirred for 2 h. The resulting mixture was filtered and dried to give the title compound as a white solid (150 g, 97.5%). $^1$H NMR (D$_2$O) δ 3.79-3.72 (m, 1H), 2.93 (dq, J=5.8, 2.8 Hz, 2H), 1.44-1.40 (m, 3H).

Preparation 14

Ethyl(S)-3-((tert-butoxycarbonyl) (1-cyanopropan-2-yl)amino) propanoate

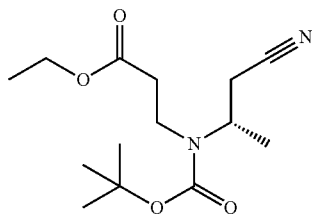 [SMILES: CCOC(=O)CCN(C(=O)OC(C)(C)C)[C@@H](C)CC#N]

A vessel was charged with EtOH (4.4 L) and (S)-3-aminobutanenitrile hydrochloride (879 g, 7.3 mol). TEA (999 g, 9.9 mol) was added dropwise followed by ethyl acrylate (918 g, 9.5 mol) while maintaining a temperature of 15-25° C. The mixture was then heated to 70-85° C. and stirred for 24 h. After this time, the mixture was cooled to 15-25° C. and TEA (852.6 g, 8.4 mol) was added dropwise followed by di-tert-butyl dicarbonate (2160.7 g, 9.9 mol) at 15-25° C. The mixture was stirred at 15~25° C. for 10 h then quenched with N-methyl piperazine (73.1 g, 0.8 mol) at 15-25° C. and stirred for 2 h. The mixture was concentrated in vacuo to 2.64 L, followed by the addition of EtOAc (4.4 L) and H$_2$O (1.76 L). 2N aqueous HCl was added until the pH of the aqueous layer was 2-3. The aqueous phase was separated, and the organic phase was washed with 15% aqueous NaCl (4.4 L). The organic phase was concentrated under reduced pressure to 2.64 L. THF (1.76 L) was added to give a solution of the title compound (4101 g, 82%). $^1$H NMR (CDCl$_3$) δ 4.02-4.18 (m, 2H), 3.37-3.45 (m, 2H), 2.48-2.58 (m, 4H), 1.44 (s, 9H), 1.29-1.30 (d, 3H, J=7 Hz), 1.21-1.24 (t, 3H, J=7 Hz).

Preparation 15 tert-Butyl(S)-5-cyano-4-hydroxy-6-methyl-3,6-dihydropyridine-1 (2H)-carboxylate

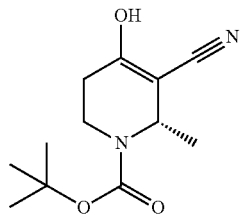 [SMILES: C[C@H]1C(C#N)=C(O)CCN1C(=O)OC(C)(C)C]

A vessel was charged with THF (12 L) and potassium t-butoxide (1042 g, 9.3 mol) and cooled to 0-5° C. Ethyl (S)-3-((tert-butoxycarbonyl) (1-cyanopropan-2-yl)amino) propanoate in THF (1200 g, 4.2 mol) was added dropwise while maintaining a temperature of 0-5° C. The mixture was stirred at 0-5° C. for 4 h and then quenched with 2N HCl until pH was 2-3. IPAc (6 L) was added. The organic phase was separated, and then washed with 15% aqueous NaCl (3.6 L). The mixture was concentrated in vacuo to 2-3 L, then IPAc (3.6 L) was added and the organic phase was washed with 15% aqueous NaCl (3.6 L). The mixture was treated with 5% activated carbon (60 g), filtered, and concentrated in vacuo to 2-3 L. Heptane (7.2 L) was added and the mixture was concentrated in vacuo again to 2-3 L. IPAc (3.6 L) was added and the mixture was heated to 50-60° C. Heptane (1.2 L) was added, then the contents were cooled to 15-25° C. Heptane (6.0 L) was added over 1 h, then the mixture was stirred for 12 h at 0-5° C. The resulting solids were filtered and washed with IPAc/heptane (0.2:1.8, 2.4L). The solid was dried under N$_2$ to give the title compound (858 g, 85%). IR (cm$^{-1}$): 3171 (broad), 2982 (sharp), 2932 (sharp), 2881 (sharp), 2219 (sharp): 1701 (sharp), 1697 (sharp), 1663 (sharp). $^1$H NMR (CDCl$_3$) δ 10.88 (s, 1H), 4.50 (s, 1H), 3.97 (s, 1H), 2.97 (s, 1H), 2.29~2.37 (m, 1H), 2.18-2.22 (m, 1H), 1.41 (s, 9H), 1.21-1.22 (d, 3H, J=6.5 Hz).

Preparation 16

1-(Diphenylmethylene)-2-(4-fluoro-3,5-dimethylphenyl) hydrazine

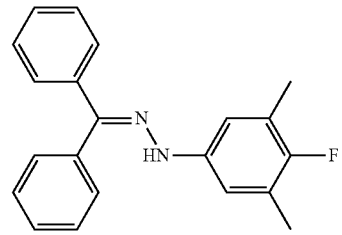 [SMILES: Cc1cc(NN=C(c2ccccc2)c2ccccc2)cc(C)c1F]

A vessel was charged with distilled tert-amyl alcohol (1.5 L), water (200 mL), 5-bromo-2-fluoro-1,3-dimethylbenzene (500 g, 2.46 mol), (diphenylmethylene) hydrazine (507 g, 2.59 mol), and NaOH (394 g, 9.85 mol). The mixture was degassed with nitrogen for 30 min, then Pd(OAc)$_2$ (0.55 g, 24.62 mmol) and Xantphos (1.4 g, 24.62 mmol) were added. The mixture was degassed with nitrogen for 30 min, then heated to 100-106° C. for 1 h. After reaction completion, the mixture was cooled to 85-95° C., and water (500 mL) was added dropwise over 1 h. The mixture was stirred for 1-2 h at 85-95° C., cooled to 65-75° C. and stirred for 1-2 h, then continued to cool to 15-25° C. and stirred for 2-4 h. The resulting cake was filtered and washed with tert-amyl alcohol (500 mL) and water (1 L). Water (2.5 L) and the wet cake were added to a vessel and slurried at 15-30° C. The contents were stirred for 2-4 h at 15-30° C., then filtered, and washed with water (1 L). The resulting solid was dried at <60° C. with nitrogen flow until the water content was ≤5.0% to give the title compound (715 g, 90%). IR (cm$^{-1}$): 3344 (sharp), 3341 (sharp), 3055 (sharp), 2952 (sharp), 2920 (sharp), 1660 (sharp), 1604 (sharp), 1579 (sharp). $^1$H NMR (CDCl$_3$) δ 7.59-7.44 (m, 5H), 7.29 (d, J=7.1 Hz, 6H), 6.69 (d, J=6.1 Hz, 2H), 2.20 (s, 6H). $^{13}$C NMR (DMSO-d$_6$) δ 143.16, 139.16, 133.52, 129.94, 129.49, 129.42, 128.72, 128.07, 126.39, 124.37, 124.19, 113.42, 113.39, 113.35, 15.10, 15.06. $^{19}$F NMR (DMSO-d$_6$) δ-134.24. TOF-MS (ESI) m/z calculated: 319.2, found 318.9 (M+H).

Preparation 17

(4-Fluoro-3,5-dimethylphenyl) hydrazine hydrochloride hydrate

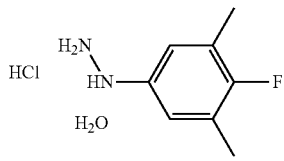

A vessel was charged with dioxane (1.05 L) and HCl gas was added at 0-30° C. until ≥20.0%. Water (98.9 g, 5.50 mol) was added into the reaction solution at 0-30° C. followed by heating to 35-45° C. 1-(Diphenylmethylene)-2-(4-fluoro-3,5-dimethylphenyl) hydrazine (700 g, 2.20 mol) was added in portions over 2 h. After completion, the mixture was cooled to 15-25° C. and stirred for 2-4 h. Filtered and washed the resulting cake with dioxane (1.4 L), then dried at ≤30° C. until dioxane is ≤1.0% to give the title compound (403 g, 87%). IR (cm$^{-1}$): 3224 (broad), 2855 (broad), 2684 (broad), 1574 (sharp). $^1$H NMR (DMSO-d$_6$) δ 10.22 (s, 3H), 6.73 (d, J=6.0 Hz, 2H), 6.05 (d, J=1.3 Hz, 1H), 3.66 (s, 4H), 2.12 (d, J=2.2 Hz, 6H). $^{13}$C NMR (DMSO-d$_6$) δ 156.19, 153.84, 141.62, 141.59, 124.59, 124.40, 115.79, 115.75, 66.81, 15.00, 14.97. $^{19}$F NMR (DMSO-d$_6$) δ-127.90. Weight percent loss 8.759% from 50° C. to 160° C. as determined by Thermogravimetric Analysis (TGA). TOF-MS (ESI) m z calculated: 155.1, found: 155.0 (M+H).

Preparation 18 tert-Butyl(S)-3-amino-2-(4-fluoro-3,5-dimethylphenyl)-4-methyl-2,4,6,7-tetrahydro-5H-pyrazolo[4,3-c]pyridine-5-carboxylate

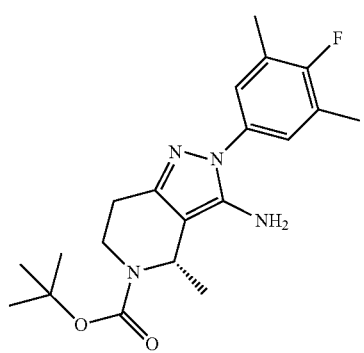 [SMILES: Cc1cc(-n2nc3c(c2N)[C@H](C)N(C(=O)OC(C)(C)C)CC3)cc(C)c1F]

A vessel was charged with NMP (1350 mL), then degassed with nitrogen for 0.5 h, before adding (4-fluoro-3,5-dimethylphenyl) hydrazine hydrochloride hydrate (274 g, 1.31 mol) and NMM (279 g, 2.77 mol). The mixture was stirred at 15-25° C. for 1 h. tert-Butyl(S)-5-cyano-4-hydroxy-6-methyl-3,6-dihydropyridine-1 (2H)-carboxylate (300 g, 1.26 mol) was added and the mixture was heated to 70-80° C. for 30 min. Upon completion, the mixture was cooled to 15-25° C. and MTBE (3 L) and 20% NH$_4$Cl (330 g of NH$_4$Cl in 1.2 L of water) were added. The mixture was stirred for 0.5 h and the layers were separated. The aqueous layer was extracted with MTBE (1.5 L). The combined layers were washed twice with 15% aqueous NaCl (247.5 g of NaCl in 1.275 L of water). The organics were concentrated in vacuo to 600 mL at ≤40° C. Heptane (2.4 L) was added to the mixture dropwise, then heated to 50-60° C. and stirred for 6 h. The mixture was then cooled to 0-5° C. over 6 h then held for 16 h at 0-5° C. The mixture was filtered and the resulting cake was washed with MTBE/n-heptane: 0.5V/3.8V. The product was dried with nitrogen flow at 25° C. to give the title compound (419.6 g, 89%). IR (cm$^{-1}$): 3448, 3375, 3129, 2960, 2926, 1682, 1637, 1589. $^1$H NMR (DMSO-d$_6$) δ 7.21 (d, J=6.4 Hz, 2H), 5.18 (s, 2H), 5.06 (d, J=43.5 Hz, 1H), 4.21-3.95 (m, 1H), 2.94 (d, J=13.5 Hz, 1H), 2.47-2.36 (m, 2H), 2.23 (d, J=2.2 Hz, 6H), 1.42 (s, 9H), 1.27-1.17 (m, 3H). 13C NMR (DMSO-d$_6$) δ 158.93, 156.53, 154.22, 141.97, 135.16, 135.13, 124.98, 124.79, 124.16, 124.11, 79.16, 44.56, 37.85, 28.63, 24.07, 14.80, 14.76. $^{19}$F NMR (DMSO-d$_6$) δ −125.12. TOF-MS (ESI) m/z calculated: 375.2, found 375.1 (M+H). Chiral purity by HPLC=100% area Preparation 19

N-(2,2-Dimethoxyethyl)-1H-imidazole-1-carboxamide

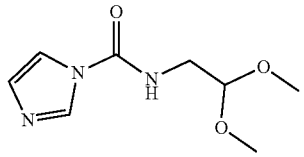

A vessel was charged with DMAc (750 mL) and CDI (181.8 g, 1.12 mol) then cooled to 0-5° C. 2,2-Dimethoxyethylamine (109.5 g, 1.04 mol) was added dropwise over 2 h at 0-5° C. then stirred at this temperature for 3 h. The reaction was monitored by NMR until no starting material remained. This solution was used as is in the subsequent step. $^1$H NMR (CDCl$_3$) δ 8.46 (t, J=5.9 Hz, 1H), 7.86 (d, J=1.2 Hz, 1H), 7.24 (d, J=1.5 Hz, 1H), 6.53 (d, J=1.3 Hz, 1H), 4.08 (t, J=5.4 Hz, 1H), 2.98 (t, J=5.6 Hz, 2H), 2.89 (s, 6H).

Preparation 20 tert-Butyl(S)-3-(3-(2,2-dimethoxyethyl) ureido)-2-(4-fluoro-3,5-dimethylphenyl)-4-methyl-2,4,6,7-tetrahydro-5H-pyrazolo[4,3-c]pyridine-5-carboxylate

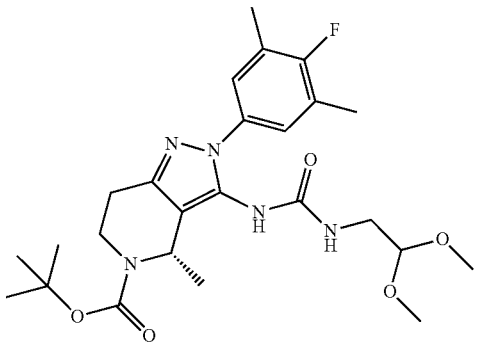 [SMILES: COC(CNC(=O)Nc1c2c(nn1-c1cc(C)c(F)c(C)c1)CCN(C(=O)OC(C)(C)C)[C@H]2C)OC]

tert-Butyl(S)-3-amino-2-(4-fluoro-3,5-dimethylphenyl)-4-methyl-2,4,6,7-tetrahydro-5H-pyrazolo[4,3-c]pyridine-5-carboxylate (300 g, 0.8 mol) in DMAc (750 mL) was added dropwise to the solution of (N-(2,2-dimethoxyethyl)-1H-imidazole-1-carboxamide at −5-5° C. Potassium t-butoxide (449.4 g, 4.0 mol) was added in 3 equal portions followed by stirring at −5-10° C. for 18 h. Water (2400 mL) was added to the mixture over 2 h at −5-10° C. tert-Butyl(S)-3-(3-(2,2-dimethoxyethyl) ureido)-2-(4-fluoro-3,5-dimethylphenyl)-4-methyl-2,4,6,7-tetrahydro-5H-pyrazolo[4,3-c]pyridine-5-carboxylate (3 g) was added as seed material and stirred for 18 h at −5-10° C. Water (1.2 L) was added to the reaction mixture over 2 h at −5-10° C. and then the slurry was stirred for 4 h at −5-10° C. The mixture was filtered and the resulting wet cake washed with water (1.8 L). The product was dried at ≤50° C. to give the title compound (321.0 g, 84%). IR (cm$^{-1}$): 3283, 3103, 2977, 2938, 2872, 2841, ~1700, 1680, 1626. $^1$H NMR (DMSO-$d_6$) δ 8.10 (s, 1H), 7.19 (d, J=6.4 Hz, 2H), 6.42 (s, 1H), 5.08 (d, J=31.3 Hz, 1H), 4.30 (t, J=5.3 Hz, 1H), 4.18 (d, J=35.0 Hz, 1H), 3.31 (s, 1H), 3.24 (s, 6H), 3.14 (s, 1H), 3.06 (s, 1H), 2.65-2.51 (m, 2H), 2.23 (d, J=2.2 Hz, 6H), 1.41 (s, 9H), 1.19 (d, J=6.6 Hz, 3H). $^{13}$C NMR (DMSO-$d_6$) δ 155.69, 155.63, 146.29, 134.74, 132.64, 124.95, 124.76, 124.61, 124.56, 114.69, 102.85, 79.39, 53.70, 41.41, 28.58, 14.79, 14.75. $^{19}$F NMR (DMSO-$d_6$) δ-123.68. TOF-MS (ESI) m z calculated: 506.3, found 505.9 (M+H). Chiral purity=100% (by HPLC).

Preparation 21 tert-Butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate

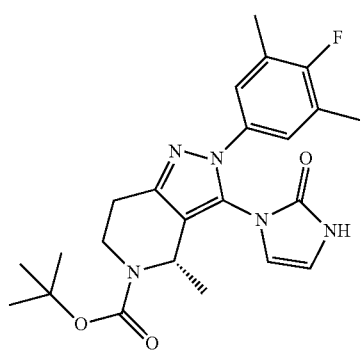 [SMILES: Cc1cc(-n2nc3c(c2-n2cc[nH]c2=O)[C@H](C)N(C(=O)OC(C)(C)C)CC3)cc(C)c1F]

A vessel was charged with THF (3.5 L) and tert-butyl(S)-3-(3-(2,2-dimethoxyethyl) ureido)-2-(4-fluoro-3,5-dimethylphenyl)-4-methyl-2,4,6,7-tetrahydro-5H-pyrazolo[4,3-c]pyridine-5-carboxylate (350 g, 0.69 mol). Methane sulfonic acid (73.2 g, 0.76 mol) was added dropwise into the mixture at 15-25° C. The mixture was heated to 40-50° C. and stirred for 18 h where HPLC showed a mixture of the title compound and the deprotected title compound. Cooled the mixture to 15-25° C., quenched with aqueous $K_3PO_4$ (147 g, dissolved in 1.4 L water), and added di-tert-butyl dicarbonate (51 g, based on the amount of deprotected intermediate according to HPLC result) at 15-25° C. then stirred for 18 h. The aqueous phase was separated and the organic phase was concentrated in vacuo to 1-1.4 L. Added IPAc (1.4 L) and 15% aqueous NaCl (1.05 L). Separated the organic phase and concentrated in vacuo to 0.7-1 L. The mixture was heated to 50-60° C. and n-heptane (2.1 L) was added dropwise over 3 h. Then, the mixture was cooled to 10-30° C., stirred for 16 h, filtered, then the resulting wet cake was washed with IPAc/n-heptane=0.2V/1.8V. The resulting material was dried at ≤50° C. to give the title compound (240 g, 78.5%).

To further purify, tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (160 g) was dissolved in EtOH (800 mL). The mixture was stirred for 2 h at 20-25° C. to obtain a solution. Water (800 mL) was added dropwise at 20-25° C. followed by 1% seed into the solution. The suspension was stirred for 16 h followed by addition of water (800 mL) at 20-25° C. over 4-10 h. The suspension was stirred for another 2-4 h, filtered, and the resulting solid washed with water (800 mL). The material was dried at ≤50° C. to give the title compound as a solid (150 g, 94%). IR (cm$^{-1}$): 3220, 3107, 2982, 2933, 2858, 1699, 1670, 1602. $^1$H NMR (CDCl$_3$) δ 10.74 (s, 1H), 7.03 (s, 2H), 6.54-6.59 (d, 2H, J=25 Hz), 5.07 (s, 1H), 4.21 (s, 1H), 3.10 (s, 1H), 2.68 (s, 2H), 2.20 (s, 6H), 1.47 (s, 9H), 1.14 (s, 3H). $^{13}$C NMR (DMSO-$d_6$) δ 159.76, 157.34, 154.00, 153.18, 146.92, 134.14, 134.11, 130.27, 125.26, 125.07, 124.30, 124.25, 112.83, 111.31, 111.17, 79.68, 28.54, 24.15, 14.81, 14.77. $^{19}$F NMR (DMSO-$d_6$) δ-122.60 Enantiomer <0.10%; Chiral purity: >99.9% by HPLC.

Preparation 22

3,6-Dibromo-2-fluorobenzaldehyde

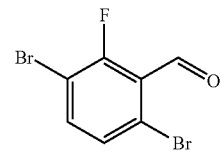 [SMILES: O=Cc1c(Br)ccc(Br)c1F]

A solution 1,4-dibromo-2-fluorobenzene (249 kg, 981 mol) was prepared in 2-MeTHF (1749 L) under nitrogen protection and the solution was polish filtered to remove any insoluble material and transferred to a holding vessel.

A solution of n-butyl lithium (697 L, 1.6M in THF) was polish filtered to remove insoluble material as it was transferred to a holding vessel.

A solution of di-isopropylamine in 2-MeTHF was prepared by adding di-isopropylamine (135 kg, 1334 mol) and 2-MeTHF (300 L). The mixture was controlled at 10-30° C. and stirred. The solution was then polish filtered to remove insoluble material and transferred to another holding vessel.

A solution of DMF in 2-MeTHF was prepared by dissolving DMF (156 kg, 2134 mol) in 2-MeTHF (499 L) and the solution was polish filtered as it was transferred to a holding vessel.

A solution of aqueous citric acid was prepared by dissolving citric acid monohydrate (748 kg, 3560 mol) in water (1830 kg) and the solution was polish filtered to remove insoluble material and transferred to a holding vessel.

Flow Reaction: A plug flow reactor consisting of pre-cooling loops for the solutions of 1,4-dibromo-2-fluorobenzene, di-isopropylamine, and DMF as well as main reactors tubing sections for the lithiation and addition to DMF was constructed and placed in a cooling bath controlled at −45 to −40° C. After the reaction feed exited the cold zone, it was quenched in another plug flow reactor with the aqueous citric acid solution and collected for batch workup. (Example flowrates: 1,4-dibromo-2-fluorobenzene=5.13 mL/min: n-butyl lithium=2.35 mL/min: di-isopropylamine=3.93 mL/min: DMF=1.81 mL/min: citric acid=6.5 mL/min)

To the quenched reaction mixture (4244 kg) was added heptane (124 kg) and the mixture was stirred then allowed to settle. The aqueous layer was removed, and the organic layer was washed with water (530 kg). The mixture was allowed to settle and the aqueous layer was removed. The organic layer was recirculated through a CUNO cartridge containing activated carbon for 8 h. The organic layer was then concentrated in vacuo to 340 L and heated to 55-65° C. After stirring at 55-65° C. for 4 h, heptane (736 kg) was added slowly at 55-65° C. and the mixture was stirred an additional 1.5 h at this temperature after completion of the heptane addition. The slurry was then cooled gradually to 0-5° C. over 7 h and stirred at that temperature for an additional 3 h. The solid was then isolated by filtration and the product cake was washed with heptane (120 kg). The solid product was then dried under vacuum to give the title compound as a solid (160.85 kg, 58%). $^1$H NMR (DMSO-$d_6$) δ 10.15 (s, 1H), 7.93 (td, J=7.8, 1.3 Hz, 1H), 7.62 (dd, J=8.6, 1.6 Hz, 1H). $^{19}$F NMR (DMSO-$d_6$) δ-109.24 (d, J=7.1 Hz). $^{13}$C NMR (DMSO-$d_6$) δ 188.41 (d, J=1.7 Hz), 158.71 (d, J=262.6 Hz), 138.98 (d, J=2.1 Hz), 131.53 (d, J=4.4 Hz), 123.89 (d, J=11.0 Hz), 123.75 (d, J=2.3 Hz), 109.73 (d, J=21.2 Hz). HRMS m/z calculated: 279.8535; found 279.8528 (M+H).

Preparation 23

(E)-1-(3,6-Dibromo-2-fluorobenzylidene)-2-methylhydrazine

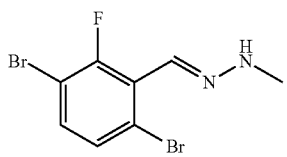

A reactor was charged with absolute EtOH (2298 L), followed by 3,6-dibromo-2-fluorobenzaldehyde (574 kg, 2036 mol) and the mixture was controlled to 15-25° C. An aqueous solution of methylhydrazine (40% w/w, 258 kg, 2240 mol) was added slowly over 4 h, after which the mixture was stirred an additional 9 h at 15-25° C. Heptane was then added (1172 kg) over 4 h, after which time the mixture was cooled to between-5 and 5° C. over 6 h, then held at that temperature for 3 h. The solid was isolated by filtration and the cake was washed with heptane (576 L). The solid was dried under vacuum for 8 h at 25-35° C. to give the title compound as a solid (443.5 kg, 70%). $^1$H NMR (CD3CN) δ 7.49-7.30 (m, 3H), 6.72 (s, 1H), 2.95 (dd, J=4.5, 1.0 Hz, 3H). 19F NMR (CD3CN) δ-106.22 (d, J=4.9 Hz). $^{13}$C NMR (CD3CN) δ 156.13 (d, J=254.6 Hz), 131.52, 129.61 (d, J=4.4 Hz), 126.05 (d, J=14.1 Hz), 125.74 (d, J=4.7 Hz), 121.76 (d, J=3.4 Hz), 108.98 (d, J=22.4 Hz), 32.75. HRMS m/z calculated: 308.9033; found 308.9036 (M+H).

Preparation 24

5-Bromo-4-fluoro-1H-indazole

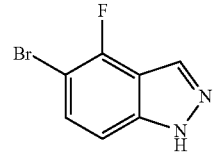 [SMILES: Fc1c(Br)ccc2[nH]ncc12]

To a solution of 4-bromo-3-fluoro-2-methylaniline (50 g, 0.245 mol) in anhydrous toluene (435 g), acetic anhydride (75 g, 0.735 mol) was added dropwise at 0-15° C. After stirring at 15-30° C. for 2-4 h a N-(4-bromo-3-fluoro-2-methylphenyl) acetamide solution was produced. The temperature was adjusted to 35-40° C. and isoamyl nitrite (57.4 g, 0.490 mol) was added dropwise below 40° C. Then, the temperature of the reaction was adjusted to 75-80° C. and the contents were stirred for 16-20 h to obtain a solution of 1-(5-bromo-4-fluoro-1H-indazol-1-yl) ethan-1-one. Cooled to 0-10° C., and added hydrochloric acid 35% (350 g) while maintaining temperature below 10° C. The temperature was adjusted to 57-63° C. and stirred for 6-10 h. Cooled the contents to 20-25° C. and stirred the slurry for 2-4 h. Filtered and rinsed the resulting wet cake with toluene (87 g). The wet cake was then added to a vessel containing water (250 g). The contents were stirred and 10% NaOH solution was added to adjust pH to 11-13 while keeping the temperature below 30° C. The slurry was cooled to 0-5° C. and stirred for 1-2 h, filtered, and the resulting wet cake was washed with water (150 g). The resulting solid was dried at 35-40° C. under vacuum to give the title compound (34 g, 65%). mp (DSC) 161.04° C.: $^1$H NMR (DMSO-$d_6$) δ 7.37-7.39 (dd, J=8.8, 1.0 Hz, 1H), 7.50-7.54 (dd, J=8.8, 6.4 Hz, 1H), 8.22 (d, J=0.8 Hz, 1H). $^{13}$C NMR (DMSO-$d_6$) δ 152.13, 149.65, 142.01, 141.93, 130.06, 129.40, 113.75, 113.51, 108.48, 108.44, 96.69, 96.50. $^{19}$F NMR (DMSO-$d_6$) δ-121.04.

Preparation 25

5-Bromo-4-fluoro-1-methyl-1H-indazole

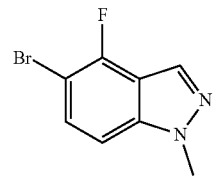

A reactor was charged with DMI (63 kg) which was degassed by sparging with nitrogen gas and then transferred to holding drums. (E)-1-(3,6-dibromo-2-fluorobenzylidene)-2-methylhydrazine (15 kg, 48.4 mol) was added to a vessel and dissolved in degassed DMI (32 kg) before being transferred to holding drums.

Fresh DMI (30 kg) was added to a vessel and the DMI was degassed by sparging with nitrogen gas. CuCl (1.3 kg, 13.1 mol) was added, followed by DBU (11.1 kg, 72.9 mol) and the mixture was further degassed with vacuum/nitrogen cycles (3 x). The mixture was heated to 70-80° C. and then the (E)-1-(3,6-dibromo-2-fluorobenzylidene)-2-methylhydrazine solution was added over 4 h. The mixture was held at 70-80° C. for 11 h, then cooled to 40-50° C. where analysis showed the reaction incomplete. The mixture was heated back to 70-80° C. for 4 h, then cooled to 40-50° C., at which time an analytical sample indicated consumption of the starting material and the mixture was cooled to 20-30° C. 2M aq. HCl (124 kg, 248 mol) was added over 6 h and the mixture was then stirred for 4 h, which caused crystallization. The solid was isolated by filtration and the cake was washed with water (59.4 kg). The solid was dried under vacuum at 35-45° C. for 25 h to give a batch of 5-bromo-4-fluoro-1-methyl-1H-indazole.

Crude 5-bromo-4-fluoro-1-methyl-1H-indazole from several production batches was pooled (471 kg, 2056 mol) and EtOAc (3296 L) was added. The reactor walls were rinsed with additional EtOAc (178 kg). Aqueous ammonium hydroxide (25% w/w, 850 kg) was added and rinsed in with water (ca. 10 kg). The mixture was controlled at 20-30° C. and stirred for 4 h, after which time it was filtered through diatomaceous earth. The diatomaceous earth was washed with additional EtOAc (118 kg) to reduce any product loss. The aqueous layer was separated, and fresh aqueous ammonium hydroxide (25% w/w; 850 kg) was added along with water (938 L). The mixture was held at 20-30° C. and stirred for 1.5 h. After settling, the aqueous layer was removed. The organic phase was circulated through a CUNO filter loaded with activated carbon for 7 h, after which the CUNO was rinsed with EtOAc (140 kg). The CUNO filtration was repeated a total of three times for the batch. The resulting solution was then concentrated to about 1650 L under vacuum. DMF (1414 L) was added and the mixture was concentrated to about 1650 L. At 45-55° C., water (1422 L) was added over 5 h. The mixture was cooled to 15-25° C. and stirred for 3 h. The solid product was isolated by filtration and the cake was washed with water (1421 kg). The product cake was dried under vacuum at 30-40° C. for 8 h, and then 35-45° C. for 16 h to give the title compound as a solid (234.1 kg, 50%). 1H NMR (DMSO-d$_6$) δ 8.08 (s, 1H), 7.46 (dd, J=8.9, 6.2 Hz, 1H), 7.37 (d, J=8.9 Hz, 1H), 4.03 (s, 3H). $^{19}$F NMR (DMSO-d$_6$) δ-112.88 (d, J=6.3 Hz). $^{13}$C NMR (DMSO-d$_6$) δ 151.11 (d, J=250.3 Hz), 141.73 (d, J=9.0 Hz), 130.29, 128.65 (d, J=2.6 Hz), 114.44 (d, J=23.5 Hz), 108.14 (d, J=4.4 Hz), 97.30 (d, J=18.8 Hz), 36.23. HRMS m z calculated: 228.9771: found: 228.9772 (M+H).

Alternative Preparation 25

To a solution of DMF (435 g) at 25-30° C. was added 5-bromo-4-fluoro-1H-indazole (20 g, 0.093 mol) and K$_2$CO$_3$ (20 g, 0.145 mol). After stirring at 25-30° C. for 30-60 min, the temperature was adjusted to 0-10° C. and then methyl iodide (17 g, 0.120 mol) was added dropwise while keeping the temperature below 10° C. After stirring at 25-30° C. for 4-6 h, water (320 g) was added while keeping the temperature below 30° C. then stirred at 25-30° C. for 2-4 h. Filtered and washed the resulting solid with water (40 g). The wet cake was added to a vessel containing DMF (38 g) and the mixture was heated to 40-50° C., then stirred for 1-2 h. Water (80 g) was added to the mixture while keeping the temperature below 50° C., then cooled to 25-30° C. over 2-3 h. Stirred at 25-30° C. for 1-2 h, filtered, and washed the wet cake with water (60 g). The solids were dried at 35-45° C. under vacuum for 12-16 h to give the title compound as a solid (12.31 g, 57.8%). mp (DSC) 106.90° C.: $^1$H NMR (CDCl$_3$) δ ppm 4.05 (s, 3H), 7.03-7.06 (dd, J=8.8, 0.8 Hz, 1H), 7.40-7.44 (dd, J=8.8, 6.2 Hz, 1H), 8.00 (d, J=0.6 Hz, 1H). 13C NMR (CDCl$_3$) δ ppm 153.29, 150.71, 141.70, 141.62, 130.75, 129.04, 129.02, 113.75, 115.34, 115.11, 106.21, 106.16, 98.10, 97.91, 36.04. $^{19}$F NMR (CDCl$_3$) δ ppm-111.32

Preparation 26 tert-Butyl(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c] pyridine-5-carboxylate

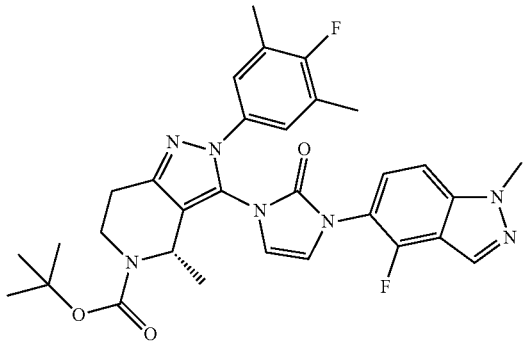 [SMILES: Cc1cc(-n2nc3c(c2-n2ccn(-c4ccc5c(cnn5C)c4F)c2=O)[C@H](C)N(C(=O)OC(C)(C)C)CC3)cc(C)c1F]

A vessel was charged with tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c] pyridine-5-carboxylate (5.034 g, 11.40 mmol), 5-bromo-4-fluoro-1-methyl-1H-indazole (3.084 g, 13.2 mmol), and powdered potassium carbonate (2.387 g, 17.27 mmol). In separate vials were added trans-N,N-dimethylcyclohexane-1,2-diamine (0.758, 5.22 mmol) and copper (I) chloride (0.229 g, 2.31 mmol) or alternatively copper (I) iodide (0.446 g, 2.34 mmol). The containers were degassed and taken into a glovebox. The vessel was fitted with a mechanical stirrer, heating mantle, and thermocouple. Degassed 1,3-dimethyl-2-imidazolidinone (20 mL) was added to the vessel, along with the trans-N,N-dimethylcyclohexane-1,2-diamine and copper (I) chloride or copper (I) iodide. The mixture was heated to 100° C. and held for 15 h. After this time, the mixture was removed from the glovebox and assayed, showing completion of the reaction. To the mixture was added EtOAc (30 mL), 12% aqueous ammonium chloride (30 mL), and methylcyclohexane (10 mL). The mixture was stirred and allowed to settle, and the aqueous phase was separated from organic phase. The organic phase was washed with another portion of 12% aqueous ammonium chloride (30 mL) and 0.5N aqueous hydrochloric acid (20 mL) sequentially. The organic phase was stirred with activated carbon (345 mg, 7 wt %) and filtered. The flask was rinsed with EtOAc (10 mL), which was then used to rinse the filter. The combined filtrates were washed with 5% aqueous sodium bicarbonate (30 mL) and water (20 mL) sequentially. The final organic phase was vacuum distilled in a 3-necked 250 mL flask at 40° C. down to 15 mL. ACN (25 mL) was added, and the mixture was again vacuum distilled down to 15 mL. ACN (25 mL) was added, and the mixture was again vacuum distilled down to 15 mL. ACN (40 mL) was added, and the mixture was vacuum distilled down to 15 mL. After the distillations, ACN (30 mL) was added to the resulting mixture. This solution was used as is in the subsequent preparation. FTIR (cm$^{-1}$): 2974.51, 1686.89, 1626.44, 1604.35, 1577.26, 1528.12, 1495.10, 1476.23, 1411.03, 1391.27, 1363.64, 1323.18, 1295.00, 1250.88, 1203.68, 1158.15, 1109.83, 1054.75, 983.02, 881.02, 860.40, 796.52, 769.36, 750.36, 719.98, 691.98, 680.53, 655.48. $^1$H NMR (DMSO-d$_6$) δ 8.3 (s, 1H), 7.65 (d, 1H, J=16.3 Hz), 7.4-7.5 (m, 1H), 7.14 (br d, J=6.1 Hz, 1H), 7.05 (d, J=2.9 Hz, 1H), 6.9-7.0 (m, 1 H), 5.2 (brs, 1H), 4.3 (brs 1 H), 4.1 (s, 3H), 2.2

(s, 6H), 1.4 (s, 9H), 1.23 (d, J-5.6 Hz, 3 H). $^{13}$C NMR (DMSO-d$_6$) δ 158.5 (d, J=243 Hz), 154.0, 151.3, 149.4 (d, J=256 Hz), 147.1, 141.8 (d, J=8.8 Hz), 134.0 (d, J=3.7 Hz), 129.7, 128.9 (d, J=2.2 Hz), 127.6 (d, J=8.1 Hz), 126.7, 125.4 (d, J=19.8 Hz), 124.1, 123.9, 115.6, 114.9, 114.8, 114.0 (d, J=21.3 Hz), 113.2, 107.2, 107.1, 106.8 (d, J=4.4 Hz), 104.9 (d, J=18.3 Hz), 79.8, 36.3, 28.5, 14.75, 14.71. $^{19}$F NMR (DMSO-d$_6$) δ–118.89, –122.46, –126.59. HRMS m z calculated: 590.2686; found: 590.2791 (M+H).

Alternative Preparation 26

A vessel was charged with tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c] pyridine-5-carboxylate (5.007 g, 11.34 mmol), 5-bromo-4-fluoro-1-methyl-1H-indazole (3.084 g, 13.2 mmol), and powdered potassium carbonate (2.356 g, 17.05 mmol). In separate vials were added trans-N,N'-dimethylcyclohexane-1,2-diamine (0.768, 5.29 mmol) and copper (I) chloride (0.226 g, 2.28 mmol) or copper (I) iodide (0.479 g, 2.52 mmol). The containers were degassed and taken into a glovebox. The vessel was fitted with a mechanical stirrer, heating mantle, and thermocouple. Degassed N-methylpyrrolidone was added to the vessel, along with the trans-N,N'-dimethylcyclohexane-1,2-diamine and copper (I) chloride or copper (I) iodide. The mixture was heated to 100° C. and held for 15 h. After this time, the mixture was removed from the glovebox and assayed, showing completion of the reaction. To the mixture was added EtOAc (30 mL), 12% aqueous ammonium chloride (30 mL), and methylcyclohexane (10 mL). The mixture was stirred and allowed to settle, and the aqueous phase was separated from organic phase. The organic phase was washed with another portion of 12% aqueous ammonium chloride (30 mL) and 0.5N aqueous hydrochloric acid (20 mL) sequentially. The organic phase was washed with water (20 mL). The final organic phase was vacuum distilled in a 3-necked 250 mL flask at 40° C. down to 15 mL. ACN (25 mL) was added, and the mixture was again vacuum distilled down to 15 mL. ACN (25 mL) was added, and the mixture was again vacuum distilled down to 15 mL. ACN (40 mL) was added, and the mixture was vacuum distilled down to 15 mL. After the distillations, ACN (40 mL) was added to the resulting mixture. This solution was used as is in the subsequent preparation. Analytical data were consistent with those collected from Preparation 26.

Preparation 27

(S)-1-(4-Fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one

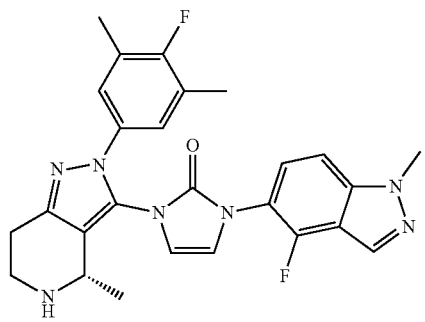 [SMILES: Cc1cc(-n2nc3c(c2-n2ccn(-c4ccc5c(cnn5C)c4F)c2=O)[C@H](C)NCC3)cc(C)c1F]

A vessel containing an ACN solution of tert-butyl(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxy late from Preparation 26 was fitted with a mechanical stirrer, heating mantle, thermocouple, and N$_2$ inlet. Methanesulfonic acid (2.054 g, 21.37 mmol) was combined with ACN (10 mL), taken up in a syringe, and added at 21° C. over 0.5 h. After the addition, the reaction mixture was heated at 30° C./h from 21° C. to 55° C. The reaction mixture reached 55° C. in 1.5 h and was held at 55° C. for another 0.5 h. After which, assay by HPLC showed complete consumption of the intermediate tert-butyl(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate. Cooled to 22° C., then added aqueous sodium hydroxide (15.779 g, 15.06 mmol) and seeds (57 mg, 1 wt %), resulting in the seeds persisting. In a separate container, aqueous sodium hydroxide (8.936 g, 8.528 mmol) was combined with water (25.019 g) and added to the slurry at 20.2° C. over 2 h. The slurry was stirred for 6 h and filtered. The wet cake was rinsed with 1:1 ACN/water (10 mL) and water (25 mL) sequentially. The wet cake was conditioned under vacuum and further dried at 55° C. in vacuo with N$_2$ purge for 12 h, to give the title compound as a solid (4.759 g, 83%). m.p. 240.14° C.-241.26° C. FTIR (cm$^{-1}$): 3278.2, 3135.5, 3099.5, 3057.9, 3042.7, 2969.7, 2960.2, 2941.1, 2923.5, 2862.7, 1705.9, 1667.5, 1644.2, 1624.2, 1598.2, 1584.2, 1573.3, 1528.2, 1493.5, 1466.1, 1448.0, 1430.2, 1394.5, 1369.6, 1357.6, 1329.9, 1313.8, 1257.0, 1238.6, 1226.6, 1214.8, 1189.2, 1171.1, 1126.5, 1105.5, 1075.8, 1058.0, 1044.5, 1015.5, 1006.1, 982.6, 965.4, 940.7, 916.7, 884.6, 874.0, 834.8, 803.8, 798.4, 774.5, 760.0, 751.9, 743.4, 722.5, 710.0, 687.5, 668.7, 641.2, 624.9, 602.1, 591.6, 555.1, 510.5; $^1$H NMR (CDCl$_3$) δ 8.09 (s, 1H), 7.42 (t, J=6.8 Hz, 1H), 7.22 (d, J=8.8 Hz, 1H), 7.10 (d, J=6.0 Hz, 1H), 6.53 (m, 1H), 6.22 (m, 1H), 4.13 (q, J=6.8 Hz, 1H), 4.08 (s, 3H), 3.36 (dt, J=4.4 Hz, 1H), 3.05 (dt, J=7.0 Hz, 1H), 2.77 (m, 2H), 2.24 (d, J=1.6 Hz, 6H), 1.29 (d, J=6.8 Hz, 3H); $^{13}$C NMR (CDCl$_3$) δ 158.87 (1JCF=243 Hz), 151.29, 149.63 (1JCF=257 Hz), 147.88, 141.42 (3 JCF=8.7 Hz), 133.45 (3 JCF=3.6 Hz), 129.70, 129.68, 128.57, 125.86, 125.37 (2JCF=19.4 Hz), 123.98 (3 JCF=5.1 Hz), 118.27, 114.77 (3JCF=10.1 Hz), 114.52 (2JCF=20.9 Hz), 114.14, 112.16, 105.43 (3 JCF=4.3 Hz), 47.03, 42.45, 35.88, 24.92, 20.29, 14.57 (3JCF=3.6 Hz); $^{19}$F NMR (36 MHZ, CDCl$_3$) δ–122.24, –126.21 (J=6.8 Hz); HRMS m z calculated: 489.2089; found: 489.2069 (M+H). Chiral purity (by HPLC): >99.9%.

Alternative Preparation 27

A vessel containing the ACN solution of tert-butyl(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate from Alternative Preparation 26 was fitted with a mechanical stirrer, heating mantle, thermocouple, and N$_2$ inlet. Methanesulfonic acid (2.107 g, 21.92 mmol) was added at 21.5° C. After the addition, the reaction mixture was heated to 75° C. and was held at 75° C. for another 0.5 h. After which, assay by HPLC showed complete consumption of the intermediate tert-butyl(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c] pyridine-5-carboxylate. Cooled to 21° C., then added aqueous sodium hydroxide (15.068 g, 15.06 mmol) and seeds (55 mg, 1 wt %), resulting in the seeds persisting. In a separate container, aqueous sodium hydroxide (9.887 g, 9.635 mmol) was combined with water (25.267 g) and added to the slurry at 22.3° C. over 2 h. The slurry was stirred for 16 h and filtered. The wet cake was rinsed with 1:1 ACN/water (10 mL) and water (25 mL) sequentially. The wet cake was conditioned under vacuum and further dried at 55° C. in vacuo with $N_2$ purge for 12 h, to give the title compound as a solid (5.206 g, 91.3%). m.p. 240.14° C.-241.26° C. FTIR (cm$^{-1}$): 3278.2, 3135.5, 3099.5, 3057.9, 3042.7, 2969.7, 2960.2, 2941.1, 2923.5, 2862.7, 1705.9, 1667.5, 1644.2, 1624.2, 1598.2, 1584.2, 1573.3, 1528.2, 1493.5, 1466.1, 1448.0, 1430.2, 1394.5, 1369.6, 1357.6, 1329.9, 1313.8, 1257.0, 1238.6, 1226.6, 1214.8, 1189.2, 1171.1, 1126.5, 1105.5, 1075.8, 1058.0, 1044.5, 1015.5, 1006.1, 982.6, 965.4, 940.7, 916.7, 884.6, 874.0, 834.8, 803.8, 798.4, 774.5, 760.0, 751.9, 743.4, 722.5, 710.0, 687.5, 668.7, 641.2, 624.9, 602.1, 591.6, 555.1, 510.5; 1H NMR (CDCl$_3$) δ 8.09 (s, 1H), 7.42 (t, J=6.8 Hz, 1H), 7.22 (d, J=8.8 Hz, 1H), 7.10 (d, J=6.0 Hz, 1H), 6.53 (m, 1H), 6.22 (m, 1H), 4.13 (q, J=6.8 Hz, 1H), 4.08 (s, 3H), 3.36 (dt, J=4.4 Hz, 1H), 3.05 (dt, J=7.0 Hz, 1H), 2.77 (m, 2H), 2.24 (d, J=1.6 Hz, 6H), 1.29 (d, J=6.8 Hz, 3H): $^{13}$C NMR (CDCl$_3$) δ 158.87 (1JCF=243 Hz), 151.29, 149.63 (1JCF=257 Hz), 147.88, 141.42 (3JCF=8.7 Hz), 133.45 (3 JCF=3.6 Hz), 129.70, 129.68, 128.57, 125.86, 125.37 (2JCF=19.4 Hz), 123.98 (3JCF=5.1 Hz), 118.27, 114.77 (3JCF=10.1 Hz), 114.52 (2JCF=20.9 Hz), 114.14, 112.16, 105.43 (3JCF=4.3 Hz), 47.03, 42.45, 35.88, 24.92, 20.29, 14.57 (3JCF=3.6 Hz); $^{19}$F NMR (36 MHz, CDCl$_3$) δ−122.24, −126.21 (J=6.8 Hz); HRMS m/z calculated: 489.2089; found: 489.2069 (M+H). Chiral purity (by HPLC): >99.9%.

Preparation 28

5-((S)-2,2-Dimethyltetrahydro-2H-pyran-4-yl)-1-((1S,2S)-1-((Z)-N'-hydroxycarbamimidoyl)-2-methylcyclopropyl)-N-methyl-N-phenyl-1H-indole-2-carboxamide

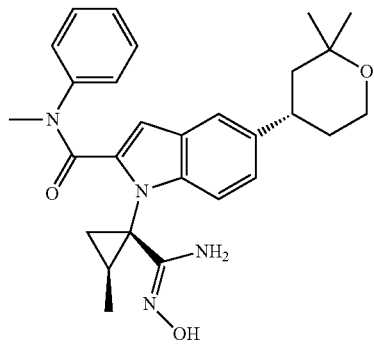 [SMILES: C[C@H]1C[C@]1(/C(N)=N/O)n1c(C(=O)N(C)c2ccccc2)cc2cc([C@H]3CCOC(C)(C)C3)ccc21]

A vessel was charged with 1-((1S,2S)-1-cyano-2-methylcyclopropyl)-5-((S)-2,2-dimethyltetrahydro-2H-pyran-4-yl)-N-methyl-N-phenyl-1H-indole-2-carboxamide (100 g, 0.23 mol) and IPA (900 mL). The mixture was heated to 65° C. over 30 min, after which a 50 wt % aqueous hydroxylamine solution (45 g: 0.68 mol) was added over 3 h. The charging container and line were rinsed with IPA (10 mL), and the reaction was stirred at 65° C. for 16 h. The reaction was cooled to 40° C. and analyzed by HPLC showing reaction completion, after which the resulting suspension was cooled to 5° C. over 3 h. The slurry was stirred at 5° C. for 5 h and filtered. The filter cake was rinsed with water (400 mL) and dried at 50° C. for 20 h until KF≤0.5% and residual IPA≤1.5% to give the title compound as a solid (102 g, 95%). mp (DSC): 229.4° C.: $^1$H NMR (CDCl$_3$) δ 7.70 (d, J=8.5 Hz, 1H), 7.39-7.30 (m, 2H), 7.27-7.09 (m, 5H), 6.40 (s, 2H), 6.00 (s, 1H), 3.88-3.72 (m, 2H), 3.67 (s, 3H), 2.99-2.84 (m, 1H), 1.78-1.51 (m, 6H), 1.36-1.32 (m, 3 H), 1.30 (s, 3H), 1.25 (s, 3H), 1.15-1.07 (m, 1H); $^{13}$C NMR (CDCl$_3$) δ 164.09, 152.20, 144.38, 138.60, 137.02, 131.04, 129.60, 127.36, 126.42, 126.24, 124.02, 118.83, 112.46, 110.37, 71.95, 61.89, 44.79, 41.00, 37.37, 33.89, 31.74, 22.40, 21.78, 17.73, 13.54. TOF-MS (ESI) m/z calculated: 475.2704, found: 475.2756 (M+H): Chiral purity (by HPLC): >99%.

Alternative Preparation 28

A vessel was charged with 1-((1S,2S)-1-cyano-2-methylcyclopropyl)-5-((S)-2,2-dimethyltetrahydro-2H-pyran-4-yl)-N-methyl-N-phenyl-1H-indole-2-carboxamide (50 g, 0.11 mol) and THF (400 mL). The mixture was heated to 30-40° C. over 30 min to afford a clear solution, after which a 50 wt % aqueous hydroxylamine solution (15 g: 0.23 mol) was added dropwise. The reaction was stirred at 30-40° C. for 6-10 h. The resulting suspension was stirred at 20-30° C. for 15 h. Water (500 mL) was added dropwise while maintaining the temperature at 20-30° C. The slurry was stirred at 20-30° C. for 6 h and filtered. The filter cake was rinsed with water (250 mL) and dried at 50° C. for 37 h until KF≤0.5% to give the title compound as a solid (52.2 g, 94.1%). Analytical data were consistent with those collected from Preparation 28.

Alternative Preparation 28

A reactor was charged with 1-((1S,2S)-1-cyano-2-methylcyclopropyl)-5-((S)-2,2-dimethyltetrahydro-2H-pyran-4-yl)-N-methyl-N-phenyl-1H-indole-2-carboxamide (5.0 g, 11.32 mmol) and THF (35.4 g). The mixture was heated to 30-40° C. to afford a light-yellow solution. A solution of 50 wt % aqueous hydroxylamine (1.50 g, 22.64 mmol) was added dropwise over 3 h, and the reaction was further stirred at 30-40° C. for 6 h. Seeds (0.05 g, 1 wt %) were added to the reaction mixture and the resulting suspension was stirred at 30-40° C. for 6 h. Water (50 g) was added at 30-40° C. at a constant rate over 8 h. The resulting slurry was cooled to 20-30° C. over 1 h and stirred for 1 h. The resulting suspension was filtered, and the filter cake was rinsed with water (4×25 mL). The wet cake was dried under vacuum at 50° C. for 40 h until KF is <0.5% to give the title compound as a solid (5.24 g, 94.2%). Analytical data were consistent with those collected from Preparation 28.

Preparation 29

5-((S)-2,2-Dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide

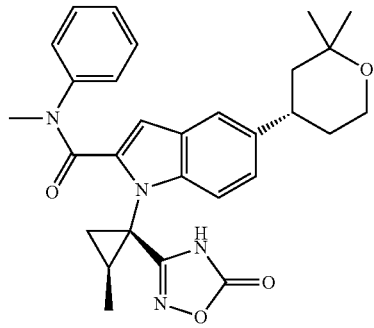 [SMILES: C[C@H]1C[C@]1(c1noc(=O)[nH]1)n1c(C(=O)N(C)c2ccccc2)cc2cc([C@H]3CCOC(C)(C)C3)ccc21]

A vessel was charged with 5-((S)-2,2-dimethyltetrahydro-2H-pyran-4-yl)-1-((1S,2S)-1-((Z)-N'-hydroxycarbamimidoyl)-2-methylcyclopropyl)-N-methyl-N-phenyl-1H-indole-2-carboxamide (100 g, 0.21 mol) and THF (400 mL). The temperature of the resulting mixture was adjusted to 20-30° C. over 10 min. CDI (68 g, 0.42 mol) was added over 10 min, followed by DBU (80 g, 0.53 mol) over 30 min. The reaction was stirred at 20-30° C. for 3-7 h. THF (400 mL) was added at 20-30° C. with stirring, and the resulting mixture was cooled to 10-20° C. over 30 min. Water (500 mL) was added over 30 min while maintaining the internal temperature at 15° C. 2N HCl solution (220 mL) was added at 15° C. over 1 h. Seed (1 g, 1 wt %) was added at 15° C. and the resulting suspension was stirred for 30 min. 2N HCl solution (680 mL) was added over 4 h at 15° C., and the resulting slurry was stirred for 12-20 h. The suspension was filtered, and the filter cake rinsed with water (500 mL). The wet cake was stirred in water (1200 mL) at 25° C. for 15 min, after which the suspension was cooled to 15° C. and stirred for 4-8 h. The suspension was filtered, and the filter cake was rinsed with water (500 mL). The solids were dried at 50-60° C. for 16-24 h until KF≤1% and residual THF≤720 ppm to give the title compound (102 g, 95%). mp (DSC): 218.28° C.: $^1$H NMR (CDCl$_3$) δ 11.40-11.16 (m, 1H), 7.56 (d, J=8.5 Hz, 1H) 7.45-7.30 (m, 3H), 7.27-7.11 (m, 4H), 5.97 (s, 1H), 3.90-3.74 (m, 2H), 3.60 (s, 3H), 3.03-2.89 (m, 1H), 1.96-1.48 (m, 8H), 1.35-1.22 (m, 9H). $^{13}$C NMR (CDCl$_3$) δ 163.80, 158.88, 157.34, 144.18, 139.61, 136.60, 130.78, 129.82, 127.96, 126.51, 126.34, 124.83, 119.56, 111.41, 110.69, 71.89, 61.79, 44.80, 37.40, 35.62, 33.82, 31.75, 23.54, 21.78, 18.15, 13.77. TOF-MS (ESI) m z calculated: 501.2496, found: 501.2541 (M+H): Chiral purity (by HPLC): >99%

Alternative Preparation 29

A reactor was charged with 1-((1S,2S)-1-cyano-2-methylcyclopropyl)-5-((S)-2,2-dimethyltetrahydro-2H-pyran-4-yl)-N-methyl-N-phenyl-1H-indole-2-carboxamide (25.0 g, 56.61 mmol) and THF (375 mL). The mixture was heated to 30-40° C. to afford a solution. A solution of 50 wt % aqueous hydroxylamine (7.50 g, 114 mmol) was added dropwise over 2 h, and the reaction was further stirred at 30-40° C. for 18 h. The temperature of the resulting reaction mixture was adjusted to 45-55° C. and concentrated under reduced pressure to 9 vol. THF (225 mL, 9 vol) was charged, and the content was concentrated under reduced pressure to 6 vol. Additional THF (225 mL, 9 vol) was charged, and the content was concentrated under reduced pressure to 6 vol. THF (225 mL, 9 vol) was charged, and the content was concentrated under reduced pressure to 6 vol. Additional THF (225 mL, 9 vol) was charged, and the content was concentrated under reduced pressure to 6 vol. THF (50 mL, 2 vol) was charged, and the mixture was heated to 65-75° C. and stirred for 30 min. The mixture was cooled to 20-30° C., charged with CDI (18.4 g, 113.5 mmol) and DBU (21.55 g, 141.6 mmol) sequentially. The reaction was stirred at 20-30° C. for 21 h. Water (125 mL) was added while maintaining the internal temperature at 10-20° C. 2N HCl solution (58 g) was added at 10-20° C. Seeds (0.3 g) were added at 10-20° C. and the resulting suspension was stirred for 1 h. 2N HCl solution (175 g) was added at 10-20° C., and the resulting slurry was stirred for 15.5 h. The suspension was filtered, and the filter cake rinsed with water (250 mL). The wet cake was stirred in water (600 mL) at 10-20° C. for 5 h and filtered. The filter cake was rinsed with water (250 mL) and dried at 55-65° C. for 72 h to constant weight to give the title compound (27.87 g, 94.4%). Analytical data were consistent with those collected from Preparation 29.

Preparation 30

5-((S)-2,2-Dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid

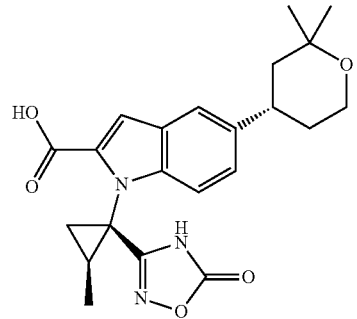 [SMILES: C[C@H]1C[C@]1(c1noc(=O)[nH]1)n1c(C(=O)O)cc2cc([C@H]3CCOC(C)(C)C3)ccc21]

A vessel was charged with 5-((S)-2,2-dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide (100 g, 0.2 mol), water (4.5 mL, 0.25 mol), and DMI (350 mL) at 25° C. The temperature was adjusted to 25° C., and sodium t-butoxide (58 g, 0.6 mol) was added. The reaction was heated to 75-85° C. over 120 min and maintained at this temperature for 10 h. The reaction mixture was cooled to 20-30° C. An 18 wt % aqueous H$_2$SO$_4$ solution (435 g, 0.8 mol) was added at <30° C., and the mixture was further diluted with IPA (200 mL). The resulting mixture was heated to 45° C. and stirred for 0.5-1 h. Water (1000 mL) was added over 2 h while maintaining the temperature at 45° C. Seeds (1 g, 1 wt %) were added, followed by the addition of water (910 mL) over 2 h while maintaining the temperature at 45° C. The resulting slurry was cooled to 25° C. over 2 h and stirred for 10 h. The suspension was filtered, and the filter cake was rinsed with water (500 mL). The solids were slurried in IPA (300 mL) and water (600 mL). The suspension was filtered, and the wet cake was dissolved in THF (660 mL) with stirring at 35-45° C. The resulting solution was concentrated to 280-380 mL. Additional THF was added and the mixture was concentrated to 330 mL of THF until KF≤0.5%. The resulting THF solution was adjusted to 45-50° C. and diluted with n-heptane (160 mL). Seeds (1 g, 1 wt %) were added and the content was stirred for 1-2 h to obtain a slurry. n-Heptane (1490 mL) was added over 2 h while maintaining the internal temperature at 45-50° C. The resulting suspension was stirred for 1-2 h, cooled to 15° C. over 2 h, and further stirred at this temperature for 12-16 h. The suspension was filtered, and the filter cake was rinsed with n-heptane (450 mL). The solids were dried at 55-65° C. for 16-18 h until residual solvent levels meet specifications (THF: NMT 720 ppm, n-heptane: NMT 0.2%, IPA: 0.5% IPA) to give the title compound as a solid (75 g, 92%). mp (DSC): 219.77° C.: $^1$H NMR (CDCl$_3$) δ 7.53 (d, J=5.0 Hz, 1H), 7.39-7.25 (m, 2H), 7.19 (d, J=4.3 Hz, 1H), 3.75-3.66 (m, 2H), 3.09-2.96 (m, 1H), 2.05-1.86 (m, 1H), 1.83-1.73 (m, 1H), 1.72-1.45 (m, 5H), 1.43-1.36 (m, 1H), 1.31-1.23 (m, 5H), 1.21-1.14 (m, 3H): $^{13}$C NMR (CDCl$_3$) δ 165.93, 161.62, 157.26, 140.12, 138.60, 128.22, 126.38, 126.28, 120.40, 113.50, 112.01, 72.01, 61.79, 44.75, 37.48, 34.67, 33.86, 31.74, 23.20, 21.81, 19.50, 14.57: TOF-MS (ESI) m/z calculated: 412.1867, found: 412.1900 (M+H): Chiral purity (by HPLC): >99.5%.

Alternative Preparation 30

A reactor was charged with 5-((S)-2,2-dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide (4.0 g, 7.99 mmol), water (0.18 mL, 9.99 mmol), and DMI (1 6 mL). NaOt-Bu (2.35 g, 24.0 mmol) was added portionwise while maintaining internal temperature at 26° C. The mixture was then stirred at 80° C. for 10 h, after which it was cooled to 25° C. and slowly quenched with 18 wt % aqueous H$_2$SO$_4$ (15.8 mL, 32.0 mmol). The resulting solution was diluted with IPA (6.40 g, 106.0 mmol) and then warmed to 45° C. Water (18.0 mL) was added over 60 min, then product seeds (40.0 mg, 0.097 mmol) were added and the resulting mixture was stirred for 45 min to afford a suspension. Water (58.4 mL) was added over 2 h, and the resulting suspension was stirred for 2 h. The slurry was cooled to 25° C., further stirred for 10 h, and filtered. The wet cake was rinsed with water (20.0 mL) and dissolved in THF (26.4 mL). The resulting solution was concentrated to ~3.3 vol, then THF (26.4 mL) was added, and the resulting solution was concentrated to ~3.3 vol, then THF (26.4 mL) was added, and the resulting solution was concentrated to ~3.3 vol. The concentrated solution was filtered, and THF (26.4 mL) was added to the filtrates. The resulting solution was concentrated to ~3.3 vol and heated to 45° C. Heptane (6.40 mL) was added, and product seeds (40.0 mg, 0.097 mmol) were added to the solution. The resulting suspension was stirred for 90 min. Heptane (59.6 mL) was added over 120 min, and the resulting slurry was stirred for an additional 90 min at 45° C. The suspension was cooled to 15° C., further stirred for 4 h, and filtered. The filter cake was rinsed with heptane (26.3 mL) and dried under vacuum at 60° C. for 18 h to give the title compound as a solid (3.04 g, 91.1%). Analytical data were consistent with those collected from Preparation 30.

Preparation 31

(1S,2S)-8'-((S)-2,2-Dimethyltetrahydro-2H-pyran-4-yl)-2-methyl-3'H,5'H-spiro [cyclopropane-1,12'-[1,2,4] oxadiazolo[4',3': 4,5] pyrazino[1,2-a] indole]-3', 5'-dione

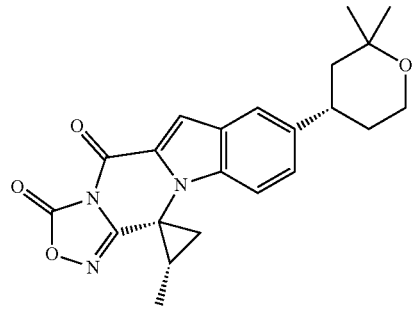 [SMILES: C[C@H]1C[C@@]12c1noc(=O)n1C(=O)c1cc3cc([C@H]4CCOC(C)(C)C4)ccc3n12]

5-((S)-2,2-Dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (15.0 g, 36.5 mmol) was suspended in EtOAc (225 mL) in a three neck round bottom flask under a nitrogen atmosphere and cooled to 0° C. N,N-Diisopropylethylamine (9.54 mL, 54.7 mmol) was added dropwise to the mixture, affording a solution. Acetyl chloride (5.19 mL, 72.9 mmol) was added dropwise over about 2 min. The mixture was stirred at ambient temperature for 1 h before concentrating under vacuum to about 100 mL. The resulting slurry was diluted with a saturated aqueous solution of NH$_4$Cl (100 mL) and stirred for 10 min. The slurry was filtered and the collected solid was slurried in aqueous NH$_4$Cl (50 mL×2) and water (50 mL×2) and filtered. The resulting solid was dried under vacuum at 55° C. The solids were further slurried in water and filtered to remove residual ammonium salts. The wet solids were then dried under full vacuum at 55° C. to give the title compound as a powder (4.83 g, 31%). $^1$H NMR (DMSO-d$_6$): δ 7.65 (s, 1H), 7.62 (s, 1H), 7.55 (d, J=8.8 Hz, 1H), 7.32 (d, J=9.2 Hz, 1H), 3.72 (d, J=8.0 Hz, 2 H), 3.16 (dd, J=7.6 Hz, 10 Hz, 1H), 3.05 (m, 1H), 2.69 (m, 1H), 1.70 (m, 2H), 1.64-1.44 (m, 3H), 1.28 (d, J=6.0 Hz, 3H), 1.31 (s, 3H), 1.19 (s, 3H). $^{13}$C NMR (DMSO-d$_6$): δ 155.9, 152.5, 151.4, 140.1, 134.2, 128.3, 128.0, 127.7, 121.1, 113.2, 110.9, 71.7, 61.1, 44.5, 42.1, 36.7, 33.8, 32.0, 25.3, 22.2, 21.3, 11.7. TOF-MS (ESI) m/z calculated: 411.2027; found: 411.2062 (M+NH$_4$+).

Preparation 32

3-((1S,2S)-1-(5-((S)-2,2-Dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one

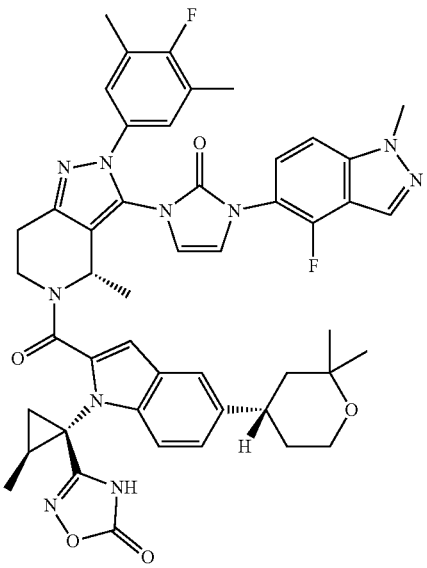 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

A vessel was charged with 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (15.08 g, 36.5 mmol) and suspended in THF (45 mL) and DMI (37.5 mL). To the flask was added HATU (15.30 g, 40.24 mmol) under $N_2$ followed by THF (15 mL) and the mixture was stirred using overhead agitation. DIPEA (14.14 g, 109.4 mmol) was added over at least 30 min while maintaining the internal temperature at 20-30° C. then stirred for 1 h. To the mixture was added(S)-1-(4-fluoro-1-methyl-1H-indazol- 5-yl)-3-(2-(4-fluoro-3,5-dimethylphenyl)-4-methyl-4,5,6,7-tetrahydro-2H-pyrazolo[4,3-c] pyridin-3-yl)-1,3-dihydro-2H-imidazol-2-one (17.6 g, 35.7 mmol) as a solid and rinsed forward with THF (15.0 mL). The reaction was stirred at ambient temperature for 42 h. EtOAc (195 mL) was added to dilute the reaction mixture, followed by sequential addition of water (45 mL) and 5 wt % aqueous solution of $Na_2SO_4$ (45 mL). The resulting biphasic mixture was stirred for at least 30 min, after which the layers were separated. The organic layer was returned to the reaction flask and 15 wt % aqueous $Na_2CO_3$ solution (150 mL) was added. The resulting biphasic mixture was stirred for at least 30 min, after which the layers were separated. The 5 wt % aqueous $Na_2SO_4$ solution (150 mL) wash process was repeated three times, and the organic layer was concentrated in vacuo at <40° C. THF (105 mL) was added, and the resulting mixture was concentrated to dryness at <40° C. again. The THF solvent swap process was repeated two more times, and the resulting solution was transferred to a reactor with temperature control. To the mixture was added formic acid (150 mL) dropwise with stirring while maintaining the internal temperature at 20-30° C. Water (195 mL) was added over 11 h, after which the resulting slurry was stirred for 8 h. The suspension was filtered, and the filter cake was rinsed with water (105 mL). The wet cake was suspended in water (300 mL) and stirred for 4 h at 40° C. The suspension was filtered, and the wet cake was rinsed with water (105 mL). The wet cake was dried in a vacuum oven at 65° C. under $N_2$ sweep for 23 h to give the title compound as a powder (27.00 g, 84%). FTIR (cm$^{-1}$): 3114.3, 2971.1, 2930.6, 2874.7, 1789.8, 1748.1, 1714.6, 1704.1, 1668.7, 1651.6, 1614.8, 1587.3, 1557.6, 1530.8, 1495.6, 1474.4, 1449.8, 1431.4, 1383.3, 1337.4, 1324.3, 1305.4, 1253.5, 1234.6, 1201.0, 118.4, 1127.3, 1106.9, 1078.7, 1058.4, 983.4, 967.6, 958.3, 931.3, 913.4, 902.4, 880.3, 859.0, 847.8, 810.7, 796.5, 771.8, 742.1, 721.8, 692.8, 681.3, 659.2: $^1$H NMR (DMSO-d$_6$) δ 8.31 (s, 1H), 7.63 (d, J=8.9 Hz, 1H), 7.57-7.23 (m, 4H), 7.20 (m, 2H), 7.09 (m, 1H), 7.02-6.69 (m, 2H), 5.89-5.14 (m, 1H), 4.94-4.31 (m, 1H), 4.11 (m, 3H), 3.80-2.70 (m, 7H), 2.25 (m, 6H), 1.85-1.34 (m, 10H), 1.27 (br s, 3H), 1.18 (br s, 6H): $^{19}$F NMR (CDCl$_3$) δ −122.2, −126.7.

Alternative Preparation 32

A vessel was charged with 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (35.04 g, 85.08 mmol), HATU (35.58 g, 93.57 mmol), THF (141 mL), and DMAc (88 mL). DIPEA (44.5 mL) was added over 30 min while maintaining the internal temperature at 20-30° C. The resulting solution was stirred for 1.5 h, after which time(S)-1-(4-fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one (37.14 g, 83.38 mmol) was added, followed by a THF (35 mL) rinse. The mixture was stirred at 20-30° C. for 45-55 h. EtOAc (490 mL), water (105 mL), and 5 wt % solution of aqueous $Na_2SO_4$ (105 mL) were added sequentially. The resulting biphasic mixture was stirred for at least 30 min before the layers were separated. The organic layer was returned to the reaction flask and 15 wt % aqueous $Na_2CO_3$ solution (350 mL) was added. The resulting biphasic mixture was stirred for at least 30 min, after which the layers were separated. The 15 wt % aqueous $Na_2CO_3$ solution (350 mL) wash process was repeated three times, and the organic layer was concentrated in vacuo to ~122.5 mL at <40° C. THF (142 g) was added, and the resulting mixture was concentrated to ~122.5 mL at <40° C. The solvent swap process was repeated two more times, and the resulting solution was transferred to a reactor with jacketed temperature control. The original reactor and transfer line were rinsed with THF (52.5 mL) and combined with the content in the reactor. The mixture was stirred at 25° C. and charged with formic acid (350 mL) over 2 h while maintaining the internal temperature at 20-30° C. Water (455 mL) was added over 6 h, after which the resulting slurry was stirred for at least 12 h. The suspension was filtered, and the filter cake was rinsed with water (245 mL). The wet cake was suspended in water (700 mL) and stirred for 6 h at 25° C. The suspension was filtered, and the wet cake was rinsed with water (245 mL). The wet cake was dried in a vacuum oven at 60° C. under $N_2$ sweep for at least 48 h to give the title compound as a powder (56.96 g, 84%). Analytical data were consistent with those collected from Preparation 31.

Alternative Preparation 32

A reactor was charged with 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (3.22 g, 7.32 mmol), THF (30 mL), DIPEA (2.84 g, 22.0 mmol), COMU (3.44 g, 8.03 mmol), and THF (3 mL). The temperature was adjusted to 20-30° C. and stirred for 1 h. (S)-1-(4-fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one (3.71 g, 7.29 mmol) and THF (6 mL) were added into the reactor. The mixture was stirred at 20-30° C. for 17 h. EtOAc (40 mL) and 5% aqueous Na₂SO₄ solution (24 mL) were added at 20-30° C. followed by 15 minutes of stirring. The layers were separated. The organics were washed sequentially with 15% aqueous Na₂CO₃ solution (40 mL), and 5% aqueous Na₂SO₄ solution (3×40 mL). The organics were concentrated in vacuo to dryness below 40° C. EtOAc (28 mL) was added to the mixture and concentrated in vacuo to dryness below 40° C. The solvent swap process was repeated two more times, then EtOAc (28 mL) was added. The temperature was adjusted to 45-55° C. followed by stirring for 0.5 h. A mixture of EtOAc (8 mL) and n-heptane (24 mL) was added into the vessel dropwise at 45-55° C. The mixture was cooled to 20-30° C. over 3.5 h then stirred for 16 h. Filtered and rinsed the cake with n-heptane (12 mL) and dried under vacuum at 50-55° C. for 20 h to give the title compound (7.03 g, 87%). Analytical data were consistent with those collected from Preparation 31.

EXAMPLE 1

3-((1S,2S)-1-(5-((S)-2,2-Dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-5-oxo-1,2,4-oxadiazol-4-ide hemi-calcium

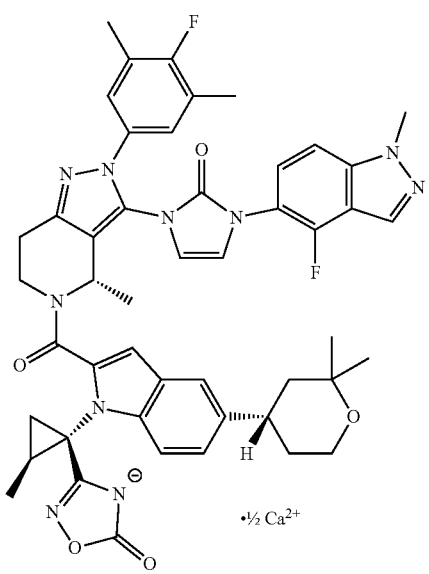 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[n-]4)C[C@@H]2C)CC3)cc(C)c1F]

To a solution of sodium hydroxide (0.55 g), water (6.6 mL), and 3A EtOH (22.5 mL) in a reactor was added 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one (7.02 g, 7.95 mmol) while maintaining the internal temperature at 20-30° C. Rinsed the charging funnel with 3A EtOH (8.4 mL) and stirred the mixture until a clear solution was obtained. A solution of calcium acetate dihydrate (0.73 g, 4.14 mmol) in water (5.3 mL) was added dropwise to obtain a turbid mixture. Dry seed (0.2 g) was added, and the resulting suspension was stirred for 10 h. Water (56.8 mL) was added to the reaction over 6 h, followed by stirring for at least 5 h. The mixture was filtered, and the cake washed with water (35 mL). The solids were dried in a vacuum oven at 55° C. with a N₂ sweep for at least 48 h to give the title compound as a free-flowing powder (6.89 g, 88.4%). TOF-MS (ESI) m/z 881.37 (M—H—Ca)

The invention claimed is:

1. A compound of the following structure:

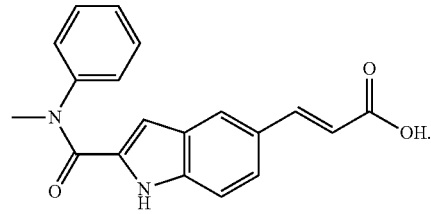 [SMILES: CN(C(=O)c1cc2cc(/C=C/C(=O)O)ccc2[nH]1)c1ccccc1]

2. A compound of the following structure:

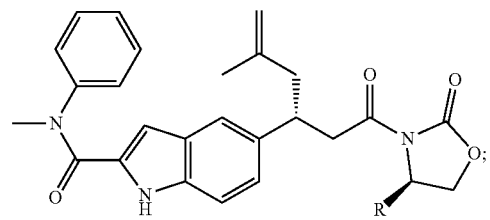

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl.

3. A compound of the following structure:

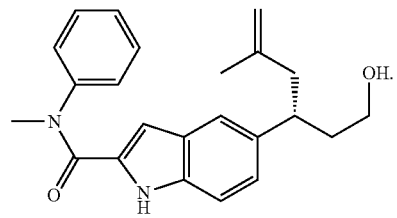 [SMILES: C=C(C)C[C@H](CCO)c1ccc2[nH]c(C(=O)N(C)c3ccccc3)cc2c1]

4. A compound of the following structure:

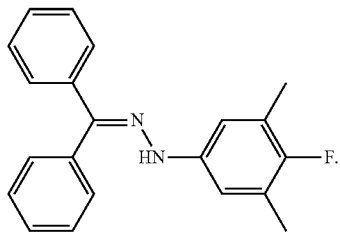 [SMILES: Cc1cc(NN=C(c2ccccc2)c2ccccc2)cc(C)c1F]

5. A process for making the compound of claim 3 of the following structure:

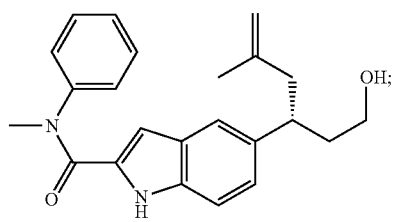 [SMILES: C=C(C)C[C@H](CCO)c1ccc2[nH]c(C(=O)N(C)c3ccccc3)cc2c1]

comprising multi-step chemical reactions starting from compound 1 of the following structure:

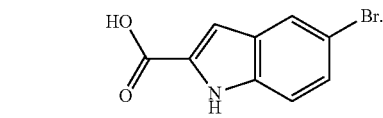

6. The process of claim 5, comprising multi-step chemical reactions starting from compound 1 and going through compound 5:

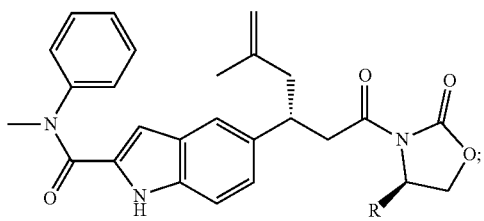

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl;
and arriving at compound 6.

7. The process of claim 6, comprising a reaction step converting compound 1 to compound 2 as shown below:

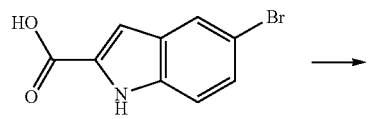

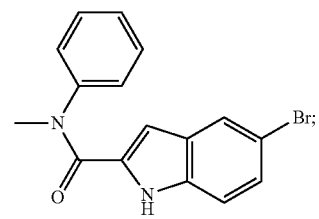

wherein the reaction is carried out in a solvent selected from toluene, MTBE, THF, 2-MeTHF, DCM, EtOAc, isobutyl acetate, isopropyl acetate, dioxane, DMF, DMAc, NMP, DMI, DMSO and CPME.

8. The process of claim 7 further comprising a reaction step converting compound 2 to compound 3 as shown below in a solvent and in the presence of a catalyst:

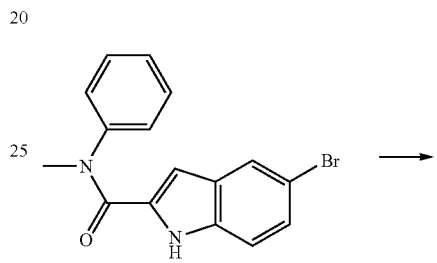

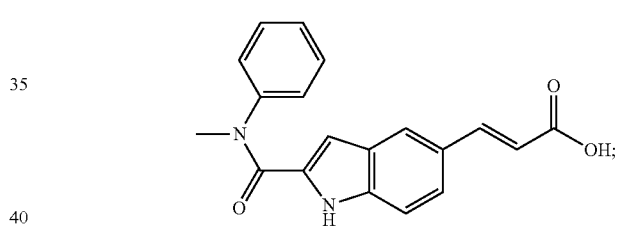

wherein the catalyst is selected from tetrakis (triphenylphosphine) [Pd(PPh$_3$)$_4$], palladium (0), palladium chloride (PdCl$_2$), palladium (II) acetate [Pd(OAc)$_2$], allylpalladium (II) chloride dimer [PdCl(C$_3$H$_5$)$_2$], Pd(dppf)Cl$_2$, Pd(dtbpf)Cl$_2$ and a combination of two or more of the listed catalysts; and wherein the solvent is selected from toluene, MeCN, MTBE, THF, 2-MeTHF, DCM, EtOAc, isobutyl acetate, isopropyl acetate, dioxane, DMF, DMAc, NMP, DMI, DMSO, and CPME.

9. The process of claim 8, further comprising a reaction step converting compound 3 to compound 4 as shown below:

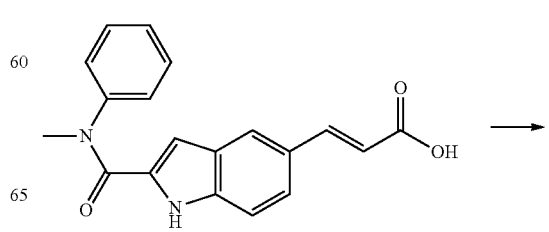

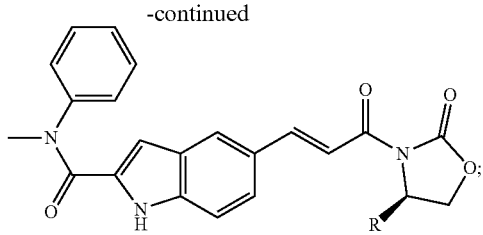

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl.

10. The process of claim 8, wherein the reaction step comprises a reaction of compound 3 with CDI in a solvent, followed by a coupling with (R)-4-phenyl-2-oxazolidone in the presence of 1,8-doazabicyclo [5.4.0]undec-7-ene in a solvent.

11. The process of claim 9, wherein the reaction step comprises a reaction of compound 3 with CDI in ACN solvent, followed by a coupling with (R)-4-benyl-2-oxazolidone in the presence of 1,8-doazabicyclo [5.4.0]undec-7-ene in N,N-dimethylacetamide solvent.

12. The process of claims 11, further comprising a reaction step converting compound 4 to compound 5 as shown below:

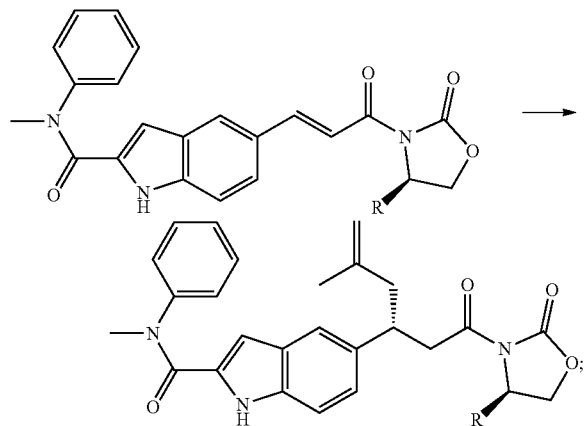

wherein R is phenyl or benzyl.

13. The process of claim 12, wherein the reaction step comprises a copper-mediated addition of 2-methyl allyl magnesium chloride, 2-methyl allyl magnesium bromide, or 2-methyl allyl magnesium iodide in the presence of lithium chloride to compound 4 to give compound 5.

14. The process of claim 13, further comprising a reaction step converting compound 5 to compound 6 as shown below:

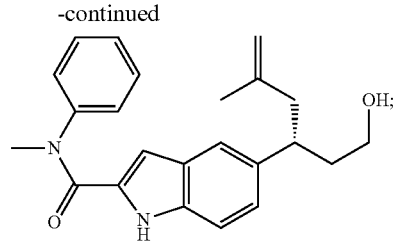

wherein R is phenyl or benzyl.

15. The process of claim 14, wherein the reaction step comprises reacting compound 5 with a reducing agent in a solvent to give compound 6;

wherein the reducing agent is selected from lithium borohydride, $NaBH_4$, BH3, LAH, $H_2$, DIBAl, and Red-Al; and wherein the solvent is selected from toluene, THF, 2-MeTHF, DCM, MTBE, and CPME.

16. The process of claim 15, comprising reaction steps as shown below:

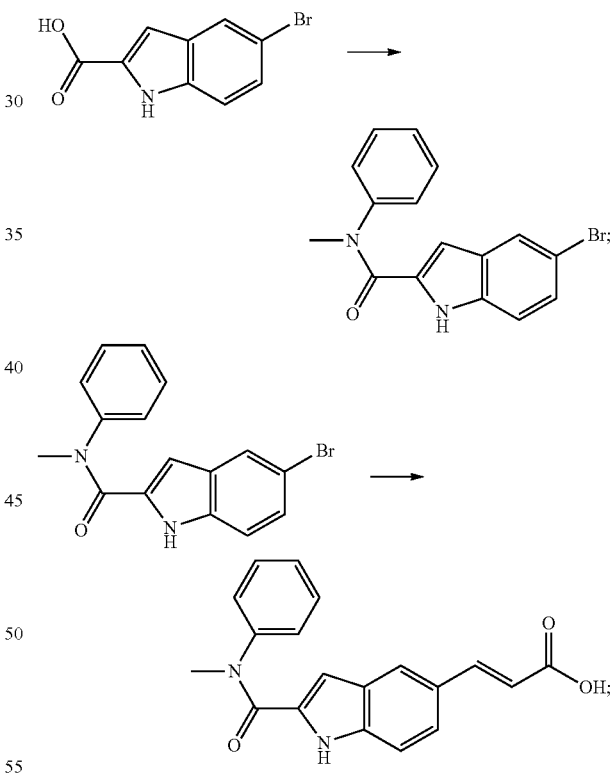

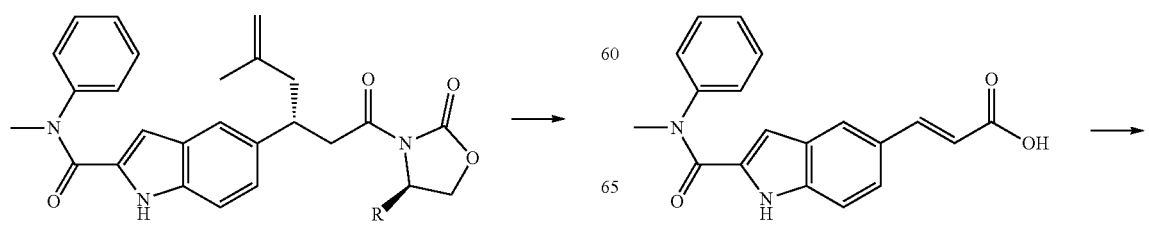

-continued

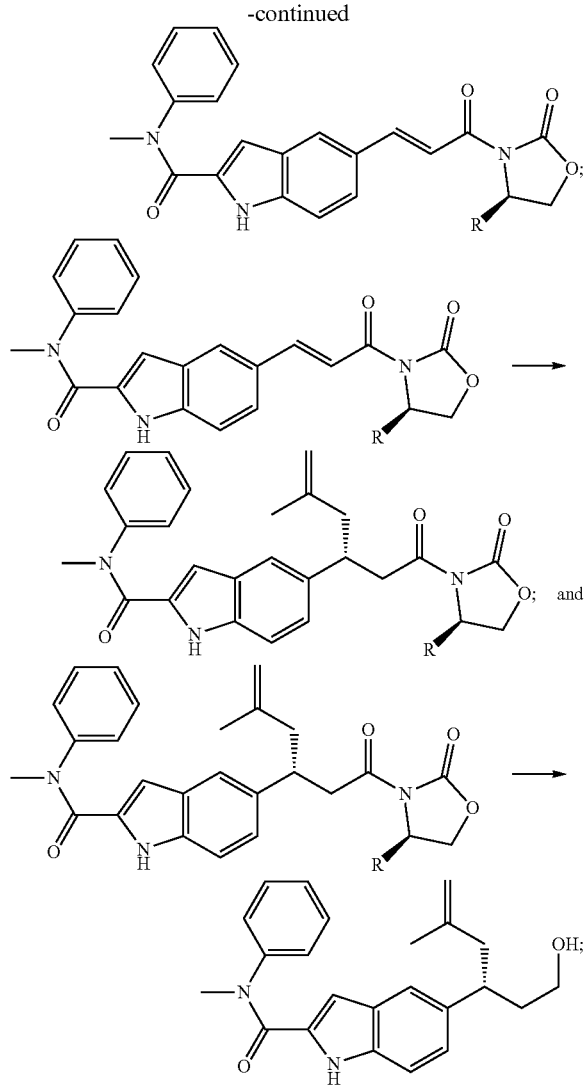

wherein R is aryl, heteroaryl, alkyl, cycloalkyl, heteroalkyl, alkenyl, heteroalkenyl, alkynyl, heteroalkynyl, arylalkyl, heteroarylalkyl, arylalkenyl, heteroarylalkenyl, arylalkynyl, or heteroarylalkynyl.

17. The process of claim 16, further comprising multi-step chemical reactions to convert compound 6 into compound 12 having the following structure:

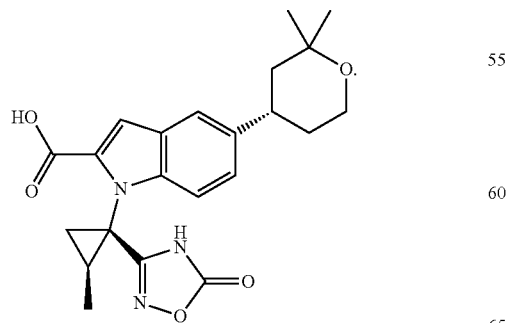

18. The process of claim 17, comprising a reaction step of converting compound 6 to compound 7 as shown below:

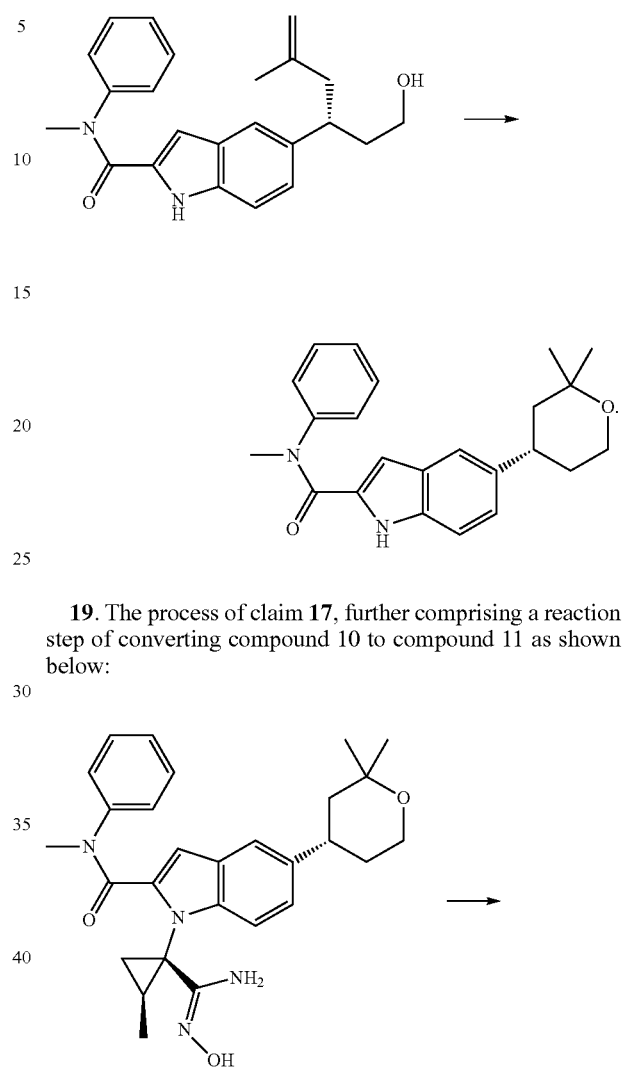

19. The process of claim 17, further comprising a reaction step of converting compound 10 to compound 11 as shown below:

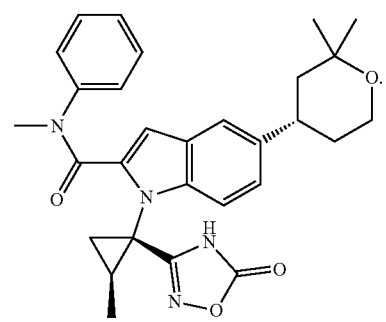

20. The process of claim 18, further comprising a reaction step of converting compound 10 to compound 11 as shown below:

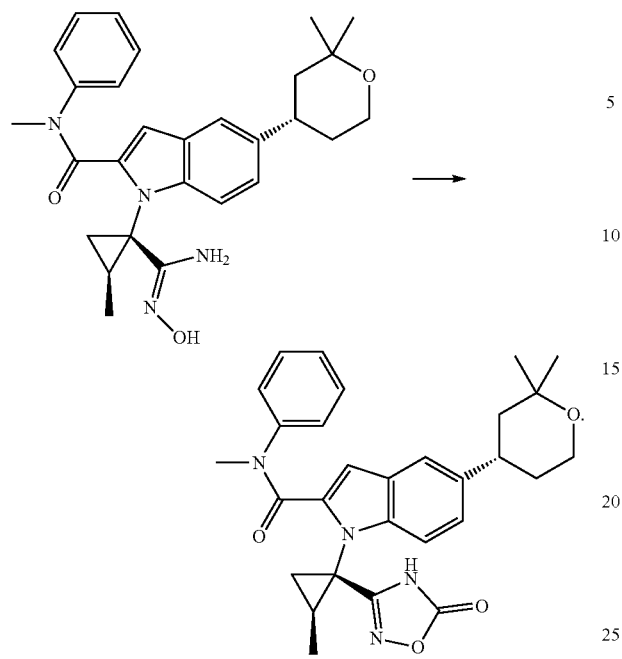

UNITED STATES PATENT AND TRADEMARK OFFICE
CERTIFICATE OF CORRECTION

| | |
|---|---|
| PATENT NO. | : 12,365,682 B2 |
| APPLICATION NO. | : 18/823214 |
| DATED | : July 22, 2025 |
| INVENTOR(S) | : Ayman D. Allian and Kenneth Derek Berglund |

It is certified that error appears in the above-identified patent and that said Letters Patent is hereby corrected as shown below:

In the Specification

In Column 2, Line 4 Delete "oxoimidazol-1-yl ]" and insert -- oxoimidazol-1-yl] --.

In Column 2, Lines 4-5 Delete "pyrazolo [4,3-c] pyridine-5-carbonyl] indol" and insert -- pyrazolo[4,3-c] pyridine-5-carbonyl]indol --.

In the Claims

In Column 63, Line 18 In Claim 10, delete "oxazolidone" and insert -- oxazolidinone --.

In Column 63, Line 19 In Claim 10, delete "doazabicyclo [5.4.0]" and insert -- diazabicyclo[5.4.0] --.

In Column 63, Line 23-34 In Claim 11, delete "benyl-2-oxazolidone" and insert -- benzyl-2-oxazolidinone --.

In Column 63, Line 24 In Claim 11, delete "doazabicyclo [5.4.0]" and insert -- diazabicyclo[5.4.0] --.

In Column 63, Line 26 In Claim 12, delete "claims" and insert -- claim --.

Signed and Sealed this
Twenty-fifth Day of November, 2025

John A. Squires
*Director of the United States Patent and Trademark Office*